(12) United States Patent
Wang et al.

(10) Patent No.: US 10,565,746 B2
(45) Date of Patent: *Feb. 18, 2020

(54) SYSTEMS AND METHODS FOR PET IMAGE RECONSTRUCTION

(71) Applicant: SHANGHAI UNITED IMAGING HEALTHCARE CO., LTD., Shanghai (CN)

(72) Inventors: Jizhe Wang, Houston, TX (US); Tao Feng, Houston, TX (US); Hongdi Li, Houston, TX (US); Wentao Zhu, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/403,594

(22) Filed: May 5, 2019

(65) Prior Publication Data

US 2019/0259185 A1 Aug. 22, 2019

Related U.S. Application Data

(63) Continuation of application No. 15/645,558, filed on Jul. 10, 2017, now Pat. No. 10,282,871.

(51) Int. Cl.
*A61B 5/05* (2006.01)
*G06K 9/00* (2006.01)
(Continued)

(52) U.S. Cl.
CPC ............ *G06T 11/003* (2013.01); *A61B 6/032* (2013.01); *A61B 6/037* (2013.01); *A61B 6/4417* (2013.01);
(Continued)

(58) Field of Classification Search
USPC ........ 382/100, 103, 106–107, 128–134, 154, 382/162, 168, 173, 181, 190, 220, 209,
(Continued)

(56) References Cited

U.S. PATENT DOCUMENTS 6,147,353 A * 11/2000 Gagnon ................. G01T 1/1648
250/363.04
6,490,476 B1 * 12/2002 Townsend .............. A61B 6/032
250/363.03
(Continued)

*Primary Examiner* — Seyed H Azarian
(74) *Attorney, Agent, or Firm* — Metis IP LLC

(57) ABSTRACT

A method may include: obtaining a 3D CT image of a scanning area of a subject; obtaining PET data of the scanning area of the subject; gating the PET data based on a plurality of motion phases; reconstructing a plurality of gated 3D PET images; registering the plurality of gated 3D PET images with a reference 3D PET image; determining a motion vector field corresponding to a gated 3D PET image of the plurality of gated 3D PET images based on the registration; determining a motion phase for each of the plurality of CT image layers; correcting, for each of the plurality of CT image layers, the CT image layer with respect to a reference motion phase; and reconstructing a gated PET image with respect to the reference motion phase based on the corrected CT image layers and the PET data.

20 Claims, 14 Drawing Sheets

(51) Int. Cl.
  *G06T 11/00* (2006.01)
  *A61B 6/03* (2006.01)
  *A61B 6/00* (2006.01)
  *G06T 7/00* (2017.01)

(52) U.S. Cl.
  CPC ............ *A61B 6/5205* (2013.01); *A61B 6/527* (2013.01); *A61B 6/5264* (2013.01); *G06T 7/0012* (2013.01); *G06T 2207/10028* (2013.01); *G06T 2207/10104* (2013.01)

(58) Field of Classification Search
  USPC ..... 382/224, 232, 254, 27, 4, 285–291, 305; 250/363.03, 363.04; 600/427, 425
  See application file for complete search history.

(56) References Cited

U.S. PATENT DOCUMENTS

| | | | |
|---|---|---|---|
| 6,841,782 B1 | 1/2005 | Balan et al. | |
| 8,569,706 B2 * | 10/2013 | Thiruvenkadam | A61B 6/037 250/363.03 |
| 9,451,926 B2 * | 9/2016 | Kinahan | A61B 6/527 |
| 9,649,509 B2 | 5/2017 | Mazin et al. | |
| 9,655,573 B2 | 5/2017 | Majewski et al. | |
| 9,706,972 B1 | 7/2017 | Ahn et al. | |
| 2003/0001097 A1 | 1/2003 | Garrard et al. | |
| 2003/0004405 A1 | 1/2003 | Townsend et al. | |
| 2003/0063787 A1 | 4/2003 | Natanzon et al. | |
| 2003/0178559 A1 | 9/2003 | Hamill et al. | |
| 2003/0179853 A1 | 9/2003 | Amemiya et al. | |
| 2003/0197128 A1 | 10/2003 | Tumer | |
| 2004/0030246 A1 | 2/2004 | Townsend et al. | |
| 2004/0044282 A1 | 3/2004 | Mixon et al. | |
| 2004/0054248 A1 | 3/2004 | Kimchy et al. | |
| 2004/0081277 A1 | 4/2004 | Amemiya et al. | |
| 2004/0081278 A1 | 4/2004 | Amemiya et al. | |
| 2005/0001170 A1 | 1/2005 | Juni | |
| 2005/0006586 A1 | 1/2005 | Balan et al. | |
| 2005/0006589 A1 | 1/2005 | Joung et al. | |
| 2005/0056788 A1 | 3/2005 | Juni | |
| 2005/0123183 A1 | 6/2005 | Schleyer et al. | |
| 2005/0123215 A1 | 6/2005 | Man | |
| 2005/0145797 A1 | 7/2005 | Oaknin et al. | |
| 2005/0173643 A1 | 8/2005 | Tumer | |
| 2005/0187465 A1 | 8/2005 | Motomura et al. | |
| 2005/0215889 A1 | 9/2005 | Patterson, II | |
| 2005/0249432 A1 | 11/2005 | Zou et al. | |
| 2006/0000983 A1 | 1/2006 | Charron et al. | |
| 2006/0033028 A1 | 2/2006 | Juni | |
| 2006/0074300 A1 | 4/2006 | Green | |
| 2006/0097175 A1 | 5/2006 | Ganin et al. | |
| 2006/0109950 A1 | 5/2006 | Arenson et al. | |
| 2006/0140335 A1 | 6/2006 | Heuscher et al. | |
| 2006/0182325 A1 | 8/2006 | Natanzon et al. | |
| 2006/0188059 A1 | 8/2006 | Amemiya et al. | |
| 2006/0208196 A1 | 9/2006 | Tumer | |
| 2007/0007455 A1 | 1/2007 | Juni | |
| 2007/0036418 A1 | 2/2007 | Pan et al. | |
| 2007/0076933 A1 | 4/2007 | Starman et al. | |
| 2007/0081704 A1 | 4/2007 | Pan et al. | |
| 2007/0116170 A1 | 5/2007 | De Man et al. | |
| 2007/0116173 A1 | 5/2007 | Arenson et al. | |
| 2007/0140409 A1 | 6/2007 | Arenson et al. | |
| 2007/0217666 A1 | 9/2007 | Gal et al. | |
| 2007/0242794 A1 | 10/2007 | Stanton et al. | |
| 2007/0242797 A1 | 10/2007 | Stewart et al. | |
| 2007/0242868 A1 | 10/2007 | Stanton et al. | |
| 2008/0042067 A1 | 2/2008 | Rousso et al. | |
| 2008/0128626 A1 | 6/2008 | Rousso et al. | |
| 2008/0156994 A1 | 7/2008 | Martin et al. | |
| 2008/0217552 A1 | 9/2008 | Tumer | |
| 2008/0240335 A1 | 10/2008 | Manjeshwar et al. | |
| 2008/0253636 A1 | 10/2008 | Deller | |
| 2008/0260228 A1 | 10/2008 | Dichterman et al. | |
| 2008/0281238 A1 | 11/2008 | Oohashi et al. | |
| 2008/0284428 A1 | 11/2008 | Fiedler et al. | |
| 2009/0080600 A1 | 3/2009 | Keller et al. | |
| 2009/0152471 A1 | 6/2009 | Rousso et al. | |
| 2009/0161931 A1 | 6/2009 | Tao et al. | |
| 2009/0175562 A1 | 7/2009 | Pan et al. | |
| 2009/0225934 A1 | 9/2009 | Hugg et al. | |
| 2009/0236532 A1 | 9/2009 | Frach et al. | |
| 2009/0237500 A1 | 9/2009 | Shao et al. | |
| 2009/0262893 A1 | 10/2009 | Stewart et al. | |
| 2009/0264753 A1 | 10/2009 | von Schulthess et al. | |
| 2009/0274272 A1 | 11/2009 | Stanton et al. | |
| 2010/0016715 A1 | 1/2010 | Gagnon et al. | |
| 2010/0158336 A1 | 6/2010 | Motomura et al. | |
| 2010/0202664 A1 | 8/2010 | Busch et al. | |
| 2010/0219863 A1 | 9/2010 | Tumer | |
| 2010/0266099 A1 | 10/2010 | Busch et al. | |
| 2010/0266171 A1 | 10/2010 | Wendler et al. | |
| 2010/0290683 A1 | 11/2010 | Demeester et al. | |
| 2010/0303319 A1 | 12/2010 | Wang | |
| 2011/0012897 A1 | 1/2011 | Stanton et al. | |
| 2011/0077506 A1 | 3/2011 | Driehuys et al. | |
| 2011/0081067 A1 | 4/2011 | Ye et al. | |
| 2011/0170757 A1 | 7/2011 | Pan et al. | |
| 2012/0078089 A1 * | 3/2012 | Wollenweber | A61B 6/5235 600/427 |
| 2012/0215090 A1 | 8/2012 | Pan et al. | |
| 2012/0219202 A1 | 8/2012 | Stanton et al. | |
| 2012/0275657 A1 | 11/2012 | Kolthammer et al. | |
| 2012/0281897 A1 | 11/2012 | Razifar et al. | |
| 2012/0321159 A1 | 12/2012 | Keller et al. | |
| 2013/0222430 A1 | 8/2013 | Bredno et al. | |
| 2013/0267830 A1 | 10/2013 | Ojha et al. | |
| 2013/0270482 A1 | 10/2013 | Jiang et al. | |
| 2013/0303898 A1 | 11/2013 | Kinahan et al. | |
| 2013/0315459 A1 | 11/2013 | Wollenweber et al. | |
| 2014/0037169 A1 | 2/2014 | Fenchel | |
| 2014/0037541 A1 | 2/2014 | Rousso et al. | |
| 2014/0079304 A1 | 3/2014 | Foo et al. | |
| 2014/0119621 A1 | 5/2014 | Uber, III | |
| 2014/0133707 A1 | 5/2014 | Park et al. | |
| 2014/0133717 A1 | 5/2014 | Kabus et al. | |
| 2014/0163368 A1 | 6/2014 | Rousso et al. | |
| 2014/0270448 A1 | 9/2014 | Mok et al. | |
| 2014/0334702 A1 | 11/2014 | El Fakhri et al. | |
| 2015/0221104 A1 | 8/2015 | Ra et al. | |
| 2015/0305701 A1 | 10/2015 | Wendler et al. | |
| 2016/0320466 A1 | 11/2016 | Berker et al. | |
| 2017/0027539 A1 | 2/2017 | Uber, III | |
| 2017/0079608 A1 | 3/2017 | Hamill | |
| 2017/0091963 A1 | 3/2017 | Panin | |
| 2017/0103523 A1 | 4/2017 | Grodzki et al. | |
| 2017/0103551 A1 | 4/2017 | Sun et al. | |
| 2017/0119330 A1 | 5/2017 | Tichauer et al. | |
| 2017/0153337 A1 | 6/2017 | Gao et al. | |
| 2017/0164912 A1 | 6/2017 | Hou et al. | |
| 2017/0176607 A1 | 6/2017 | Liu et al. | |
| 2017/0176610 A1 | 6/2017 | An et al. | |
| 2017/0209225 A1 | 7/2017 | Wu | |
| 2017/0215830 A1 | 8/2017 | Henning et al. | |
| 2017/0228896 A1 | 8/2017 | Yu et al. | |
| 2018/0174333 A1 | 6/2018 | Feng et al. | |
| 2018/0174360 A1 | 6/2018 | Feng et al. | |

* cited by examiner

600

- 610 — Obtaining a plurality of CT images corresponding to a scanning area of a subject
- 620 — Obtaining PET data corresponding to the same scanning area of the subject
- 630 — Gating the PET data to reconstruct a plurality of gated PET images corresponding to different respiratory phases of the subject
- 640 — Registering the gated PET images
- 650 — Determining a motion vector field based on the registration
- 660 — For each of the plurality of CT images, determining the respiratory phase of the CT image
- 670 — For each of the plurality of CT images, correcting the CT image, based on a deformation vector filed corresponding to the determined respiratory phase of the CT image
- 680 — Reconstructing a PET image based on the corrected CT images and the PET data

SYSTEMS AND METHODS FOR PET IMAGE RECONSTRUCTION

CROSS-REFERENCE TO RELATED APPLICATIONS

This application is a Continuation of U.S. patent application Ser. No. 15/645,558, filed on Jul. 10, 2017, the entire contents of which are hereby incorporated by reference.

TECHNICAL FIELD

The present disclosure generally relates to systems and methods for image processing, and more specifically relates to methods and systems for reconstructing PET image.

BACKGROUND

Positron emission tomography (PET) is a specialized radiology procedure that generates three-dimensional images of functional processes in a target organ or tissue of a body. Specifically, in PET studies, a biologically active molecule carrying a radioactive tracer is first introduced into a subject's body. The PET system then detects pairs of gamma rays emitted indirectly by the tracer and reconstructs a three-dimensional image of the tracer concentration within the body by analyzing the detected signals. Because the biologically active molecules used in PET studies are natural substrates of metabolism at the target organ or tissue, PET can evaluate the physiology (functionality) of the target organ or tissue, as well as its biochemical properties. Changes in these properties of the target organ or tissue may provide information for the identification of the onset or progression of a disease before an anatomical change relating to the disease become detectable by other diagnostic tests, such as computed tomography (CT) or magnetic resonance imaging (MRI).

Furthermore, the high sensitivity of PET—in the picomolar range—may allow the detection of small amounts of radio-labeled markers in vivo. PET may be used in conjunction with other diagnostic tests to achieve simultaneous acquisition of both structural and functional information of the body of a subject. Examples include a PET/CT hybrid system, a PET/MR hybrid system.

A PET/CT image may be obtained using a PET/CT hybrid system. During a scan in the PET/CT system, a subject may undergo respiratory motion, which may cause artifact in an image. The PET data may be corrected based on the CT data in order to compensate for the attenuation of the PET projection data caused by loss of detection of true coincidence events. A PET image may be obtained based on the corrected PET data. To this end, the CT data and the PET data may need to be matched with respect to the scanning of a same area of a subject; a mismatch may subsequently cause artifacts in the PET image, which in turn may affect an interpretation of the PET image, or diagnose on the basis of the PET image. During a scanning of the subject by the PET/CT hybrid system, if the scanning is operated for chest or upper abdomen examinations, respiratory motion of the lungs and/or cardiac motion of the heart of the subject may lead to the mismatch. Thus, it is desirable to develop a method and system for matching such acquired CT data and PET data to reduce the effect of respiratory and/or cardiac motion of the subject and improve the quality of a PET image reconstructed accordingly.

SUMMARY

According to an aspect of the present disclosure, a method may include: obtaining a 3D CT image of a scanning area of a subject, the 3D CT image including a plurality of CT image layers, a CT image layer corresponding to a group of spatial points relating to the subject; obtaining PET data of the scanning area of the subject, the PET data corresponding to a first motion signal with a plurality of motion phases of the subject; gating the PET data based on the plurality of motion phases of the first motion signal; reconstructing, based on the gated PET data, a plurality of gated 3D PET images, a gated 3D PET image corresponding to one of the plurality of motion phases, a gated 3D PET image including a plurality of gated PET image layers, a gated PET image layer corresponding to a group of spatial points relating to the subject; registering the plurality of gated 3D PET images with a reference 3D PET image; determining, based on the registration, a motion vector field corresponding to a gated 3D PET image of the plurality of gated 3D PET images, a motion vector field corresponding to a motion phase; determining, for each of the plurality of CT image layers, a motion phase based on the motion phases of the plurality of gated 3D PET images; correcting, for each of the plurality of CT image layers, based on a motion vector field of a gated 3D PET image corresponding to the same motion phase as the CT image layer with respect to a gated 3D PET image corresponding to a reference motion phase, the CT image layer with respect to the reference motion phase; and reconstructing a gated PET image with respect to the reference motion phase based on the corrected CT image layers and the PET data.

In some embodiments, the determining the motion phase for each of the plurality of CT image layers based on the motion phases of the plurality of gated 3D PET images may include: identifying, from each of the plurality of gated 3D PET image, a gated PET image layer corresponding to same group of spatial points as the CT image layer; determining a similarity between the CT image layer and each of the plurality of identified gated PET image layers; and designating one of the motion phases of the plurality of gated 3D PET images as the motion phase of the CT image layer based on its similarities with the plurality of identified gated PET image layers.

In some embodiments, the designating one of the motion phases of the plurality of gated 3D PET images as the motion phase of the CT image layer based on its similarities with the plurality of identified gated PET image layers may include: identifying a highest similarity among the determined similarities between the CT image layer and the plurality of identified gated PET image layers; and designating the motion phase of the gated 3D PET image including the identified gated PET image layer having the highest similarity as the motion phase of the CT image.

In some embodiments, the determining the similarity between the CT image layer and each of the plurality of identified gated PET image layers may be based on at least one of a pixel-based similarity, an entropy-based similarity, a mutual information similarity, and a contour-based similarity.

In some embodiments, wherein the determining the motion phase for each of the plurality of CT image layers based on the motion phases of the plurality of gated 3D PET images may include: obtaining a second motion signal during a scanning that provides the 3D CT image, wherein the second motion signal is of a same type as the first motion signal; and determining the motion phase of the CT image layer based on the motion phases of the plurality of gated 3D PET images and the second motion signal.

In some embodiments, the second motion signal may be obtained from an external device.

In some embodiments, the plurality of motion phases of the first motion signal may be determined based on an amplitude or a time interval of a motion presented in the motion signal.

In some embodiments, the registering the plurality of gated 3D PET images with a reference 3D PET image may be based on at least one of an optical flow registration algorithm, demons registration algorithm, or a B-spline registration algorithm.

In some embodiments, the correcting, for each of the plurality of CT image layers, based on a motion vector field of a gated 3D PET image corresponding to the same motion phase as the CT image layer with respect to a gated 3D PET image corresponding to a reference motion phase, the CT image layer with respect to the reference motion phase may include: determining a deformation vector field for the CT image layer based on the motion vector field of the gated 3D PET image corresponding to the same motion phase as the CT image layer with respect to a gated 3D PET image corresponding to a reference motion phase; and correcting the CT image layer with respect to the reference motion phase based on the deformation vector field.

In some embodiments, the reconstructing the gated PET image with respect to the reference motion phase based on the corrected CT image layers and the PET data may include: determining an attenuation map based on the corrected CT image layers; and reconstructing the gated PET image with respect to the reference motion phase based on the attenuation map and the PET data.

In some embodiments, the motion vector field may include a plurality of motion vectors, the motion vector representing a motion of a spatial point of the subject from a gated 3D PET image to another gated 3D PET image.

In some embodiments, the plurality of motion phases of the first motion signal may be determined based on an amplitude or a time interval of a motion presented in the first motion signal.

In some embodiments, a CT image layer of the plurality of CT image layers may be a transverse slice of the 3D CT image, and a gated PET image layer may be a transverse slice of a gate 3D PET image.

In some embodiments, the reference motion phase may be one of the plurality of motion phases of the subject According to another aspect of the present disclosure, a system may include at least one processor; and storage for storing instructions, the instructions, when executed by the at least one processor, causing the system to perform a method. The method may include: obtaining a 3D CT image of a scanning area of a subject, the 3D CT image including a plurality of CT image layers, a CT image layer corresponding to a group of spatial points relating to the subject; obtaining PET data of the scanning area of the subject, the PET data corresponding to a first motion signal with a plurality of motion phases of the subject; gating the PET data based on the plurality of motion phases of the first motion signal; reconstructing, based on the gated PET data, a plurality of gated 3D PET images, a gated 3D PET image corresponding to one of the plurality of motion phases, a gated 3D PET image including a plurality of gated PET image layers, a gated PET image layer corresponding to a group of spatial points relating to the subject; registering the plurality of gated 3D PET images with a reference 3D PET image; determining, based on the registration, a motion vector field corresponding to a gated 3D PET image of the plurality of gated 3D PET images, a motion vector field corresponding to a motion phase; determining, for each of the plurality of CT image layers, a motion phase based on the motion phases of the plurality of gated 3D PET images; correcting, for each of the plurality of CT image layers, based on a motion vector field of a gated 3D PET image corresponding to the same motion phase as the CT image layer with respect to a gated 3D PET image corresponding to a reference motion phase, the CT image layer with respect to the reference motion phase; and reconstructing a gated PET image with respect to the reference motion phase based on the corrected CT image layers and the PET data.

In some embodiments, the determining the motion phase for each of the plurality of CT image layers based on the motion phases of the plurality of gated 3D PET images may include: identifying, from each of the plurality of gated 3D PET image, a gated PET image layer corresponding to same group of spatial points as the CT image layer; determining a similarity between the CT image layer and each of the plurality of identified gated PET image layers; and designating one of the motion phases of the plurality of gated 3D PET images as the motion phase of the CT image layer based on its similarities with the plurality of identified gated PET image layers; and the correcting, for each of the plurality of CT image layers, based on a motion vector field of a gated 3D PET image corresponding to the same motion phase as the CT image layer with respect to a gated 3D PET image corresponding to a reference motion phase, the CT image layer with respect to the reference motion phase may include: determining a deformation vector field for the CT image layer based on the motion vector field of the gated 3D PET image corresponding to the same motion phase as the CT image layer with respect to a gated 3D PET image corresponding to a reference motion phase; and correcting the CT image layer with respect to the reference motion phase based on the deformation vector field.

In some embodiments, the designating one of the motion phases of the plurality of gated 3D PET images as the motion phase of the CT image layer based on its similarities with the plurality of identified gated PET image layers may include: identifying a highest similarity among the determined similarities between the CT image layer and the plurality of identified gated PET image layers; and designating the motion phase of the gated 3D PET image including the identified gated PET image layer having the highest similarity as the motion phase of the CT image.

In some embodiments, the determining the motion phase for each of the plurality of CT image layers based on the motion phases of the plurality of gated 3D PET images may include: obtaining a second motion signal during a scanning that provides the 3D CT image, wherein the second motion signal is of a same type or can be transformed to a same type as the first motion signal; and determining the motion phase of the CT image layer based on the motion phases of the plurality of gated 3D PET images and the second motion signal, wherein the first motion signal is obtained based on the PET data.

In some embodiments, the system may be further caused to superimpose a gated 3D image and a corrected 3D CT image of a same motion phase to obtain a superimposed 3D image.

According to another aspect of the present disclosure, a method may include: obtaining a 3D CT image of a scanning area of a subject, the 3D CT image including a plurality of CT image layers, a CT image layer corresponding to a group of spatial points relating to the subject; obtaining PET data of the scanning area of the subject, the PET data corresponding to a first motion signal with a plurality of motion phases of the subject; gating the PET data based on the plurality of motion phases of the first motion signal; reconstructing, based on the gated PET data, a plurality of gated 3D PET images, a gated 3D PET image corresponding to one of the plurality of motion phases, a gated 3D PET image including a plurality of gated PET image layers, a gated PET image layer corresponding to a group of spatial points relating to the subject; registering the plurality of gated 3D PET images with a reference 3D PET image; determining, based on the registration, a motion vector field corresponding to a gated 3D PET image of the plurality of gated 3D PET images, a motion vector field corresponding to a motion phase; determining, for each of the plurality of CT image layers, a motion phase based on the motion phases of the plurality of gated 3D PET images; and correcting, for each of the plurality of CT image layers, based on a motion vector field of a gated 3D PET image corresponding to the same motion phase as the CT image layer with respect to a gated 3D PET image corresponding to a reference motion phase, the CT image layer with respect to the reference motion phase.

According to another aspect of the present disclosure, a non-transitory storage medium may include a set of instructions, wherein when executed by at least one processor, the set of instructions may direct the at least one processor to perform acts of: According to an aspect of the present disclosure, a method may include: obtaining a 3D CT image of a scanning area of a subject, the 3D CT image including a plurality of CT image layers, a CT image layer corresponding to a group of spatial points relating to the subject; obtaining PET data of the scanning area of the subject, the PET data corresponding to a first motion signal with a plurality of motion phases of the subject; gating the PET data based on the plurality of motion phases of the first motion signal; reconstructing, based on the gated PET data, a plurality of gated 3D PET images, a gated 3D PET image corresponding to one of the plurality of motion phases, a gated 3D PET image including a plurality of gated PET image layers, a gated PET image layer corresponding to a group of spatial points relating to the subject; registering the plurality of gated 3D PET images with a reference 3D PET image; determining, based on the registration, a motion vector field corresponding to a gated 3D PET image of the plurality of gated 3D PET images, a motion vector field corresponding to a motion phase; determining, for each of the plurality of CT image layers, a motion phase based on the motion phases of the plurality of gated 3D PET images; correcting, for each of the plurality of CT image layers, based on a motion vector field of a gated 3D PET image corresponding to the same motion phase as the CT image layer with respect to a gated 3D PET image corresponding to a reference motion phase, the CT image layer with respect to the reference motion phase.

In some embodiments, the acts may further comprise reconstructing a gated PET image with respect to the reference motion phase based on the corrected CT image layers and the PET data.

According to another aspect of the present disclosure, a system may include an acquisition module, and a processing module. The acquisition module may be configured to obtain a 3D CT image of a scanning area of a subject, the 3D CT image including a plurality of CT image layers, a CT image layer corresponding to a group of spatial points relating to the subject, and obtain PET data of the scanning area of the subject, the PET data corresponding to a first motion signal with a plurality of motion phases of the subject. The processing module may include a gating unit, a reconstruction unit, a registration unit, a motion vector field determination unit, a motion phase determination unit, and a motion deformation processing unit. The gating unit may be configured to gating the PET data based on the plurality of motion phases of the first motion signal. The reconstruction unit may be configured to reconstruct, based on the gated PET data, a plurality of gated 3D PET images, a gated 3D PET image corresponding to one of the plurality of motion phases, a gated 3D PET image including a plurality of gated PET image layers, a gated PET image layer corresponding to a group of spatial points relating to the subject. The registration unit may be configured to register the plurality of gated 3D PET images with a reference 3D PET image. The motion vector field determination unit may be configured to determine, based on the registration, a motion vector field corresponding to a gated 3D PET image of the plurality of gated 3D PET images, a motion vector field corresponding to a motion phase. The motion phase determination unit may be configured to, for each of the plurality of CT image layers, determine a motion phase based on the motion phases of the plurality of gated 3D PET images. The motion deformation processing unit may be configured to correct, for each of the plurality of CT image layers, based on a motion vector field of a gated 3D PET image corresponding to the same motion phase as the CT image layer with respect to a gated 3D PET image corresponding to a reference motion phase, the CT image layer with respect to the reference motion phase.

In some embodiments, the reconstruction unit may be configured to reconstruct a gated PET image with respect to the reference motion phase based on the corrected CT image layers and the PET data.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 6A and FIG. 6B illustrate flowcharts illustrating exemplary processes for processing image data according to some embodiments of the present disclosure;

FIG. 11A-1 through FIG. 11A-3 and FIG. 11B-1 through FIG. 11B-3 illustrate gated PET images of two different respiratory phases reconstructed overlapped with the same attenuation map without correction according to some embodiments of the present disclosure;

FIG. 13A-1 through FIG. 13A-3 and FIG. 13B-1 through FIG. 13B-3 illustrate a gated PET image overlapped with an attenuation map without correction and with a corrected attenuation map, respectively, according to some embodiments of the present disclosure.

DETAILED DESCRIPTION

Figure 1:
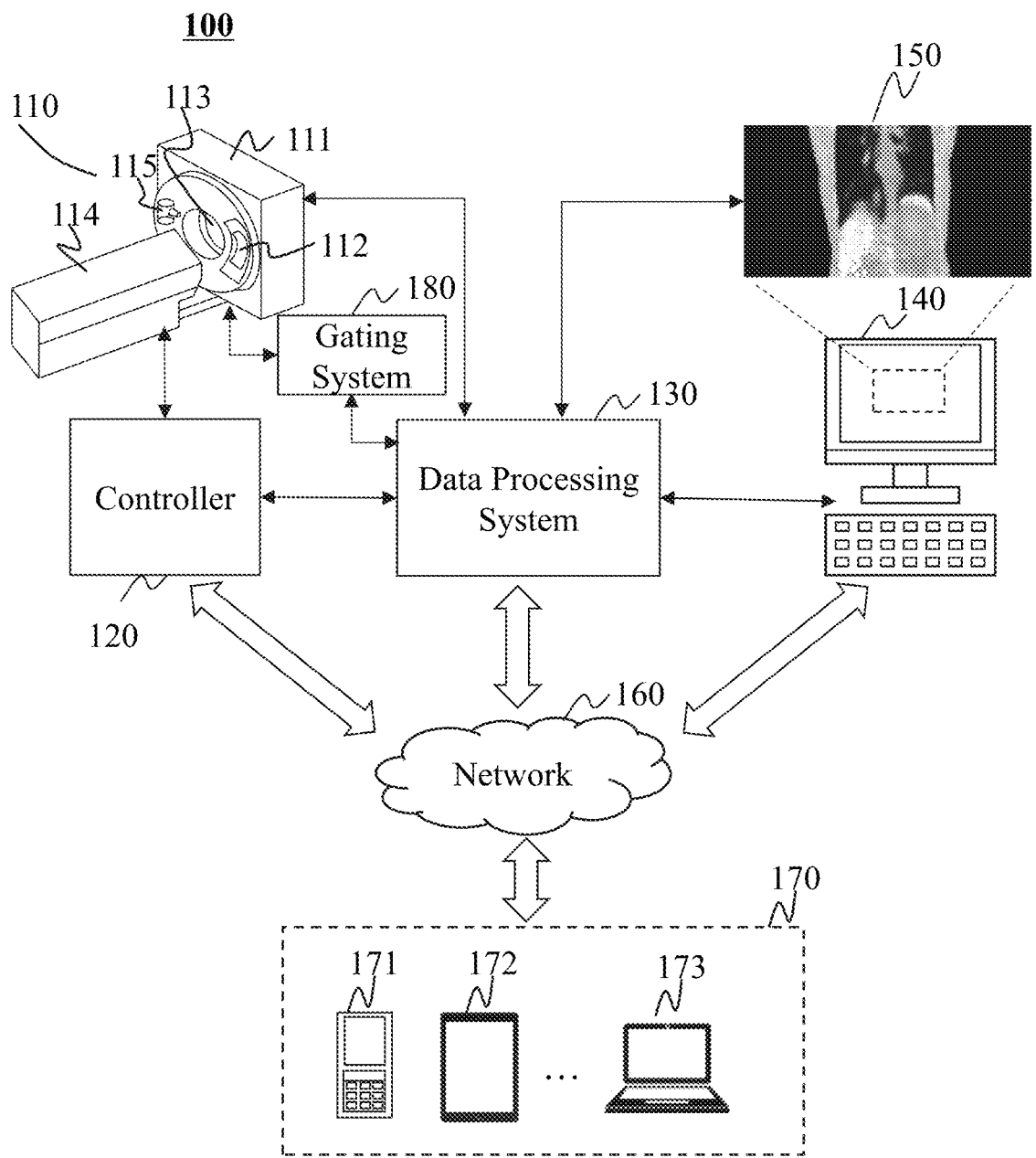
FIG. 1 is a schematic diagram illustrating an exemplary imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an erasable programmable read-only memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging, such as for disease diagnosis or research purposes. In some embodiments, the imaging system may be a computed tomography (CT) system, an emission computed tomography (ECT) system, a magnetic resonance imaging (MRI) system, an ultrasonography system, an X-ray photography system, a positron emission tomography (PET) system, or the like, or any combination thereof.

The following description is provided to help better understanding CT/PET image reconstruction methods and/or systems. The term "image" used in this disclosure may refer to a 2D image, a 3D image, a 4D image, and/or any related image data (e.g., CT data, projection data corresponding to the CT data). This is not intended to limit the scope the present disclosure. For persons having ordinary skills in the art, a certain amount of variations, changes, and/or modifications may be deducted under the guidance of the present disclosure. Those variations, changes, and/or modifications do not depart from the scope of the present disclosure.

FIG. 1 illustrates an exemplary imaging system according to some embodiments of the present disclosure. An imaging system may produce an image of a subject. As illustrated, the imaging system may include an imaging device 110, a controller 120, a data processing system 130, an input/output device 140, a network 160, and a terminal(s) 170.

In some embodiments, the imaging device 110 may scan a subject, and generate a plurality of data relating to the subject. The data processing system 130 may reconstruct an image from the plurality of data. In some embodiments, the imaging device 110 may be a medical imaging device, for example, a PET device, a SPECT device, a CT device, an MRI device, or the like, or any combination thereof (e.g., a PET-CT device, a PET-MRI device, or a CT-MRI device). In some embodiments, the imaging device 110 may include a scanner to scan a subject and obtain information relating to the subject. In some embodiments, the imaging device 110 may be a radioactive scanning device. The radioactive scanning device may include a radioactive scanning source to emit radioactive rays to the subject being scanned. The radioactive rays may include, for example, particle rays, photon rays, or the like, or any combination thereof. The particle rays may include neutron, proton, electron, μ-meson, heavy ion, or the like, or any combination thereof. The photon rays may include X-ray, γ-ray, α-ray, β-ray, ultraviolet, laser, or the like, or any combination thereof. In some embodiments, the photon ray may be X-ray, and the imaging device 110 may be a CT system, a digital radiography (DR) system, a multi-modality system, or the like, or any combination thereof. Exemplary multi-modality system may include a computed tomography-positron emission tomography (CT/PET) system, a computed tomography-magnetic resonance imaging (CT-MRI) system, or the like.

In some embodiments, the imaging device 110 may be the CT/PET imaging device including a gantry 111, a detector 112, a detecting region 113, a table 114, and a radioactive scanning source 115. The gantry 111 may support the detector 112 and the radioactive scanning source 115. A subject may be placed on the table 114 for scanning. The radioactive scanning source 115 may emit radioactive rays to the subject. The detector 112 may detect radiation events (e.g., gamma photons) emitted from the detecting region 113. In some embodiments, the detector 112 may include one or more detector units. The detector 112 may include a scintillation detector (e.g., a cesium iodide detector), a gas detector, etc. The detector 112 may be and/or include a single-row detector in which a plurality of detector units are arranged in a single row and/or a multi-row detector in which a plurality of detector units are arranged in multiple rows.

The controller 120 may control the imaging device 110, the input/output device 140, and/or the data processing system 130. In some embodiments, the controller 120 may control the X-ray generating unit and/or the X-ray detecting unit (if any) of the imaging device 110. The controller 120 may receive information from or send information to the imaging device 110, the input/output device 140, and/or the data processing system 130. For example, the controller 120 may receive commands from the input/output device 140 provided by a user. As another example, the controller 130 may process data input by a user via the input/output unit 140 and transform the data into one or more commands. As a further example, the controller 120 may control the imaging device 110, the input/output device 140, and/or the data processing system 130 according to the received commands or transformed commands. As still a further example, the controller 120 may receive image signals or data related to a subject from the imaging device 110. As still a further example, the controller 120 may send image signals or data to the data processing system 130. As still a further example, the controller 120 may receive processed data or constructed image from the data processing system 130. As still a further example, the controller 120 may send processed data or constructed image to the input/output device 140 for displaying. In some embodiments, the controller 120 may include a computer, a program, an algorithm, a software, a storage device, one or more interfaces, etc. Exemplary interfaces may include the interfaces with the imaging device 110, the input/output device 140, the data processing system 130, and/or other modules or units in the imaging system.

In some embodiments, the controller 120 may receive a command provided by a user including, for example, an imaging technician, a doctor, etc. Exemplary commands may relate to a scan time, a location of the subject, the location of a couch on which the subject lies, subjection or a rotating speed of the gantry, a specific parameter relating to a threshold that may be used in the image reconstruction process, or the like, or any combination thereof. In some embodiments, the controller 120 may control the data processing system 130 to select different algorithms to process the raw data of an image.

The data processing system 130 may process information received from the imaging device 110, the controller 120, the input/output device 140, and/or the terminal 170. In some embodiments, the data processing system 130 may generate one or more CT images based on the information. The data processing system 130 may deliver the images to the input/output device 140 for display. In some embodiments, the data processing system 130 may perform operations including, for example, data preprocessing, image reconstruction, image correction, image composition, lookup table creation, or the like, or any combination thereof. In some embodiments, the data processing system 130 may process data based on an algorithm including, for example, the Fourier slice theorem, a filtered back projection algorithm, fan-beam reconstruction, iterative reconstruction, or the like, or any combination thereof. Merely by way of example, image data regarding a lung may be processed in the data processing system 130. In some embodiments, the data processing system 130 may generate a reconstructed PET image based on a CT image. In some embodiments, artifacts may appear in the PET image because of the mismatch of the PET data and CT data. The data processing system 130 may apply various algorithms or techniques to reduce the artifacts. For example, the projection data relating to the chest of the object may be processed to reduce the artifacts.

For brevity, an image, or a portion thereof (e.g., a region of interest (ROI) in the image) corresponding to an object (e.g., a tissue, an organ, a tumor, etc., of a subject (e.g., a patient, etc.)) may be referred to as an image, or a portion of thereof (e.g., an ROI) of or including the object, or the object itself. For instance, an ROI corresponding to the image of a lung or a heart may be described as that the ROI includes a lung or a heart. As another example, an image of or including a chest may be referred to a chest image, or simply a chest. For brevity, that a portion of an image corresponding to an object is processed (e.g., extracted, segmented, etc.) may be described as the object is processed. For instance, that a portion of an image corresponding to a lung is extracted from the rest of the image may be described as that the lung is extracted.

In some embodiments, the data processing system 130 may generate a control signal relating to the configuration of the imaging device 110. In some embodiments, the result generated by the data processing system 130 may be provided to other modules or units in the system including, e.g., a database (not shown), a terminal (not shown) via the network 160. In some embodiments, the data from the data processing system 130 may be transmitted to a storage (not shown) for storing.

The input/output device 140 may receive or output information. In some embodiments, the input/output device 140 may include a keyboard, a touch screen, a mouse, a remote controller, or the like, or any combination thereof. The input and/or output information may include programs, software, algorithms, data, text, number, images, voices, or the like, or any combination thereof. For example, a user may input some initial parameters or conditions to initiate an imaging process. As another example, some information may be imported from an external resource including, for example, a floppy disk, a hard disk, a wired terminal, a wireless terminal, or the like, or any combination thereof. The output information may be transmitted to a display, a printer, a storage device, a computing device, or the like, or a combination thereof. In some embodiments, the input/output device 140 may include a graphical user interface. The graphical user interface may facilitate a user to input parameters, and intervene in the data processing procedure.

The network 160 may include any suitable network that can facilitate exchange of information and/or data for the imaging system 100. In some embodiments, one or more components of the imaging system 100 (e.g., the imaging device 110, the controller 120, the data processing system 130, the input/output device 140, and/or the terminal 170, etc.) may communicate information and/or data with one or more other components of the imaging system 100 via the network 160. For example, the data processing system 130 may obtain image data from the imaging device 110 via the network 160. As another example, the data processing system 130 may obtain user instructions from the terminal 170 via the network 160.

The network 160 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 160 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 160 may include one or more network access points. For example, the network 160 may include wired and/or wireless network access points such as base stations and/or internet exchange points through which one or more components of the imaging system 100 may be connected to the network 160 to exchange data and/or information.

The terminal(s) 170 may include a mobile device 171, a tablet computer 172, a laptop computer 173, or the like, or any combination thereof. In some embodiments, the mobile device 171 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 170 may be part of the data processing system 130.

The gating system 180 may collect information relating to, for example, breathing, heartbeat, etc. The gating system 180 may analyze the information to obtain a motion signal including, for example, a respiration signal, a cardiac motion signal, etc. The gating system may include a gating camera for detecting motion of the subject, a control panel, a marker fixed on surface of the subject for indicating motion of the subject, or the like, or any combination thereof. In some embodiments, the gating camera may be an infrared camera. For example, when the imaging device 110 is scanning the patient, the gating system may be triggered automatically. The gating system may collect information associated with respiration motion. The data collected by the gating system may be stored together with the PET data or CT data.

In some embodiments, the imaging device 110, the controller 120, the data processing system 130, the input/output device 140, the terminal 170, and the gating system 180 may be connected to or communicate with each other directly. In some embodiments, the imaging device 110, the controller 120, the data processing system 130, the input/output device 140 may be connected to or communicate with each other via a network 160. In some embodiments, the imaging device 110, the controller 120, the data processing system 130, the input/output device 140 may be connected to or communicate with each other via an intermediate unit (not shown in FIG. 1). The intermediate unit may be a visible component or an invisible field (radio, optical, sonic, electromagnetic induction, etc.). The connection between different units may be wired or wireless. The wired connection may include using a metal cable, an optical cable, a hybrid cable, an interface, or the like, or any combination thereof. The wireless connection may include using a Local Area Network (LAN), a Wide Area Network (WAN), a Bluetooth, a ZigBee, a Near Field Communication (NFC), or the like, or any combination thereof. The network 160 that may be used in connection with the present system described herein are not exhaustive and are not limiting.

The CT/PET system described herein is merely provided for illustrating an example of the imaging device 110, and not intended to limit the scope of the present application. The CT/PET system may find its applications in different fields such as, for example, medicine or industry. As another example, the imaging device 110 may be used in internal inspection of components including e.g., flaw detection, security scanning, failure analysis, metrology, assembly analysis, void analysis, wall thickness analysis, or the like, or any combination thereof.

It should be noted that the above description about the imaging system is merely an example, and should not be understood as the only embodiment. To those skilled in the art, after understanding the basic principles of the connection between different units, the units and connection between the units may be modified or varied without departing from the principles. The modifications and variations are still within the scope of the current application described above. In some embodiments, these units may be independent, and in some embodiments, part of the units may be integrated into one unit to work together.

Figure 2:
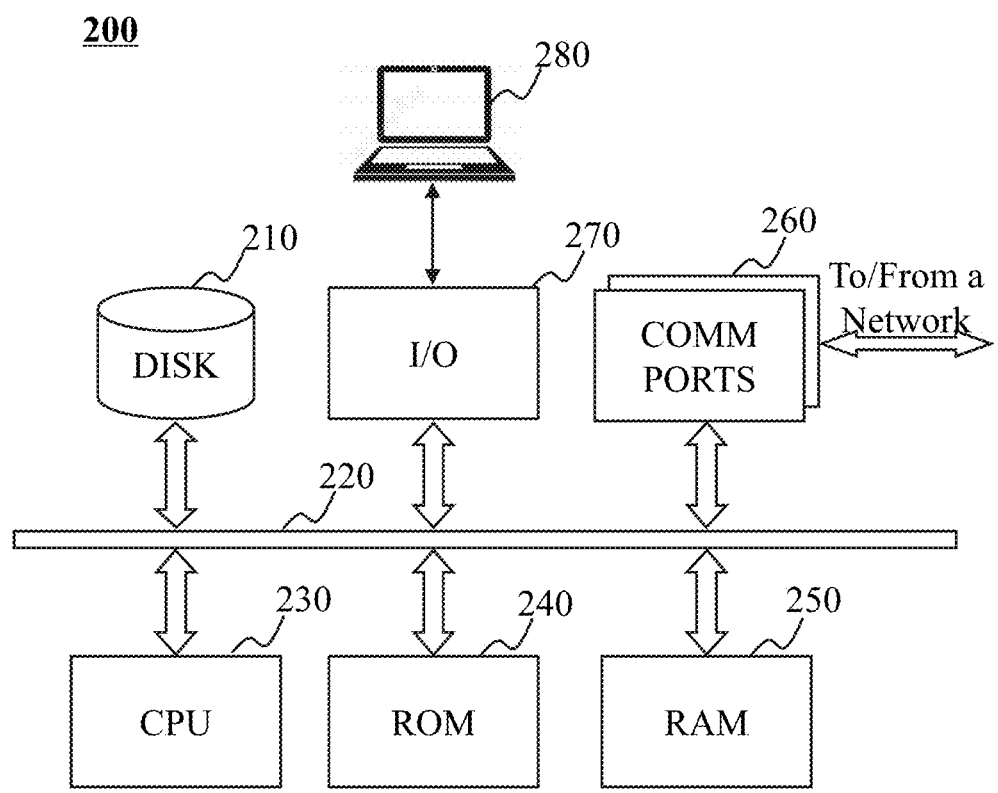
FIG. 2 is a schematic diagram illustrating exemplary hardware and software components of a computing device on which data processing system, may be implemented according to some embodiments of the present disclosure.

FIG. 2 is a schematic diagram illustrating exemplary hardware and software components of a computing device 200 on which data processing system 130, may be implemented according to some embodiments of the present disclosure. For example, the processing module 440 may be implemented on the computing device 200 and configured to perform functions of the data processing system 130 described in this disclosure.

The computing device 200 may be a general purpose computer or a special purpose computer, both may be used to implement an on-demand system for the present disclosure. The computing device 200 may be used to implement any component of the on-demand service as described herein. For example, the data processing system 130 may be implemented on the computing device 200, via its hardware, software program, firmware, or any combination thereof. Although only one such computer is shown, for convenience, the computer functions relating to the on-demand service as described herein may be implemented in a distributed fashion on a number of similar platforms, to distribute the processing load.

The computing device 200, for example, may include COM ports 260 connected to and from a network connected thereto to facilitate data communications. The computing device 200 may also include a central processing unit (CPU) 230, in the form of one or more processors, for executing program instructions. The exemplary computer platform may include an internal communication bus 220, program storage and data storage of different forms, for example, a disk 210, and a read only memory (ROM) 240, or a random access memory (RAM) 250, for various data files to be processed and/or transmitted by the computer. The exemplary computer platform may also include program instructions stored in the ROM 240, RAM 250, and/or other type of non-transitory storage medium to be executed by the CPU 230. The methods and/or processes of the present disclosure may be implemented as the program instructions. The computing device 200 also includes an I/O component 270, supporting input/output between the computer and other components therein such as user interface elements 280. The computing device 200 may also receive programming and data via network communications.

Merely for illustration, only one CPU and/or processor is described in the computing device 200. However, it should be noted that the computing device 200 in the present disclosure may also include multiple CPUs and/or processors, thus operations and/or method steps that are performed by one CPU and/or processor as described in the present disclosure may also be jointly or separately performed by the multiple CPUs and/or processors. For example, if in the present disclosure the CPU and/or processor of the computing device 200 executes both operation A and operation B, it should be understood that operation A and operation B may also be performed by two different CPUs and/or processors jointly or separately in the computing device 200 (e.g., the first processor executes operation A and the second processor executes operation B, or the first and second processors jointly execute operations A and B).

Figure 3:
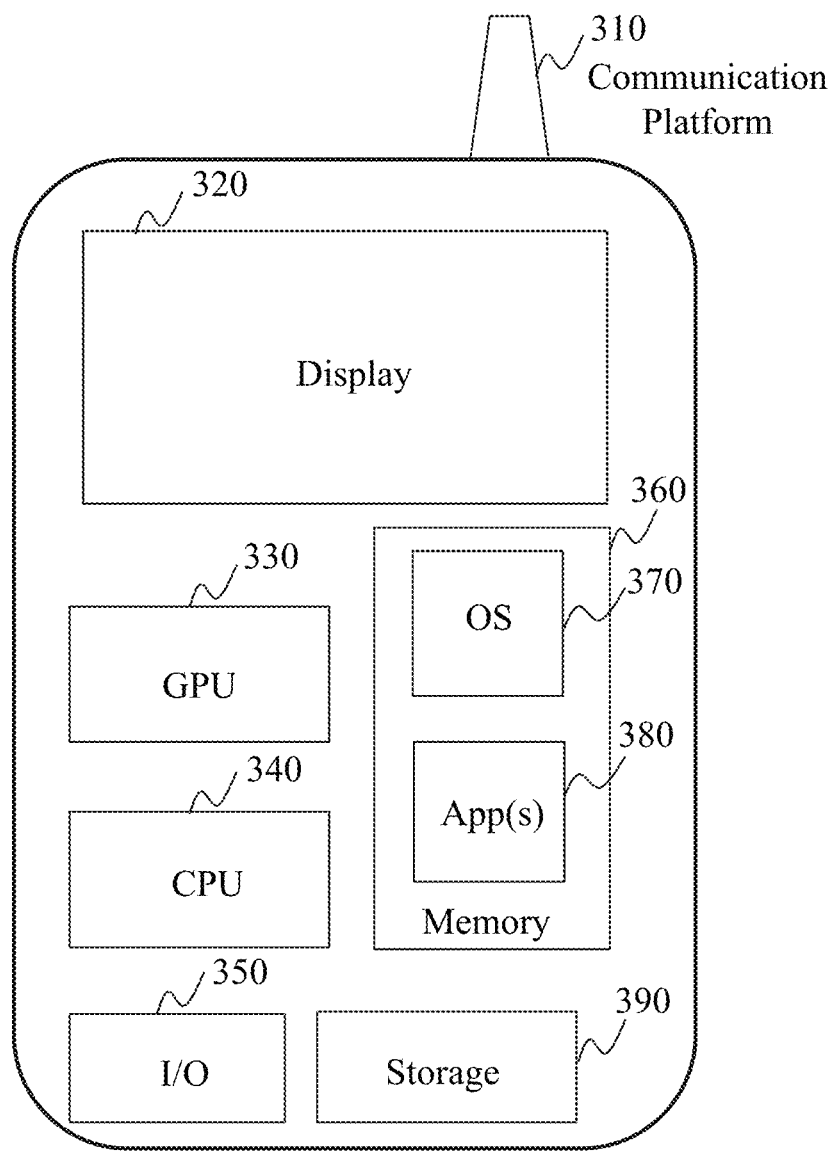
FIG. 3 is a schematic diagram illustrating exemplary hardware and/or software components of an exemplary mobile device on which a user terminal may be implemented according to some embodiments of the present disclosure.

FIG. 3 is a schematic diagram illustrating exemplary hardware and/or software components of an exemplary mobile device 300 on which a user terminal may be implemented according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, an operation system (OS) 370, applications 380, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the data processing system 130. User interactions with the information stream may be achieved via the I/O 350 and provided to the data processing system 130 and/or other components of the imaging system 100 via the network 160.

Figure 4:
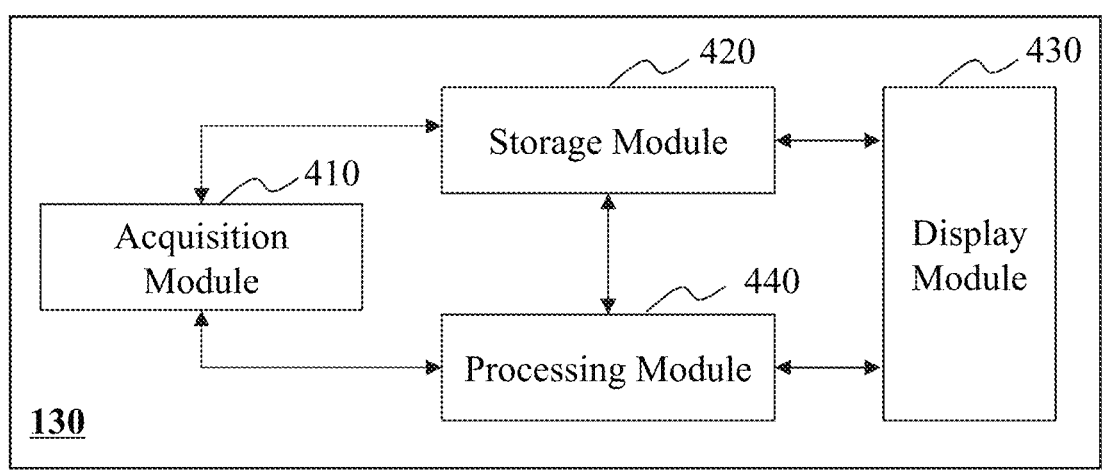
FIG. 4 is a block diagram illustrating an exemplary data processing system according to some embodiments of the present disclosure.

FIG. 4 is a block diagram illustrating an exemplary data processing system 130 according to some embodiments of the present disclosure. As shown in FIG. 4, the data processing system 130 may include a data acquisition module 410, a storage module 420, a display module 430, and a processing module 440. At least a portion of the data processing system 130 may be implemented on a computing device as illustrated in FIG. 2, or a mobile device as illustrated in FIG. 3.

The data acquisition module 410 may acquire data. The data acquired may be generated from the imaging device 110, or the controller 120. In some embodiments, the data may be acquired from an external data source via the network 160. The data acquired may be 3D image data, and/or 2D image data. The data acquired may include information regarding a whole human body, a lung, a bronchus, a thorax, or the like, or any combination thereof. In some embodiments, the data acquisition module 410 may include a wireless receiver to receive data via the network 160.

The storage module 420 may store data. The data stored may be a numerical value, a signal, an image, information of a subject, an instruction, an algorithm, or the like, or a combination thereof. The data stored may be acquired by the data acquisition module 410, imported via the input/output device 140, generated in the processing module 440, or pre-stored in the storage module 420 during system initialization or before an operation of data processing. The storage module 420 may include a system storage (e.g., a disk) that is provided integrally (i.e. substantially non-removable), or a storage that is removably connectable to the system via, for example, a port (e.g., a UBS port, a firewire port, etc.), a drive (a disk drive, etc.), etc. The storage module 420 may include, for example, a hard disk, a floppy disk, selectron storage, random access memory (RAM), dynamic random access memory (DRAM), static random access memory (SRAM), bubble memory, thin film memory, magnetic plated wire memory, phase change memory, flash memory, a cloud disk, or the like, or a combination thereof. The storage module 420 may be connected to or communicate with one or more of the data acquisition module 410, the processing module 440, and the display module 430. In some embodiments, the storage module 420 may be operationally connected with one or more virtual storage resources (e.g., cloud storage, a virtual private network, other virtual storage resources, etc.) via the network 160.

The display module 430 may display information. The information displayed may include a value, a text, an image, and information of a subject. The information displayed may be transmitted from the data acquisition module 410, the storage module 420, and/or the processing module 440. In some embodiments, the display module 430 may transform information to the input/output device 140 for display. In some embodiments, the display module 430 may transform the image data that is generated from the processing module 440 for display. In some embodiments, the display module 430 may transform the image data directly extracted from the storage module 420 or the network 160 for display.

The processing module 440 may process data and construct an image. The data may be acquired from the data acquisition module 410, the storage module 420, etc. The image constructed may be transmitted by the processing module 440 to the display module 430. In some embodiments, the data processed may be acquired from an external data source via the network 160. In some embodiments, the processing module 440 may reconstruct image data to generate one or more images. The image data may be reconstructed by using a reconstruction algorithm. The reconstruction algorithm may be an analytic reconstruction algorithm, an iterative reconstruction algorithm, or based on compressed sensing (CS). In some embodiments, the processing module 440 may segment the image data to obtain an image of a specific portion of a subject, for example, a heart, a blood vessel, a lung, a bronchus, or the like, or any combination thereof.

In some embodiments, the processing module 440 may include a universal processor, e.g., a programmable logic device (PLD), an application-specific integrated circuit (ASIC), a microprocessor, a system on chip (SoC), a digital signal processor (DSP), or the like, or any combination thereof. Two or more of these universal processors in the processing module 440 may be integrated into a hardware device, or two or more hardware devices independently with each other. It should be understood, the universal processor in the processing module 440 may be implemented via various methods. For example, in some embodiments, the processing procedure of the processing module 440 may be implemented by hardware, software, or a combination of hardware software, not only by a hardware circuit in a programmable hardware device in an ultra large scale integrated circuit, a gate array chip, a semiconductor such a transistor, or a field programmable gate array, a programmable logic device, and also by a software performed by various processors, and also by a combination of the hardware and the software above (e.g., firmware).

It should be noted that the above description about the data processing system 130 is merely an example, and should not be understood as the only embodiment. To those skilled in the art, after understanding the basic principles of the connection between different units, the units and connection between the units may be modified or varied without departing from the principles. The modifications and variations are still within the scope of the current application described above. For example, the display module 430 may be unnecessary before image displaying in the input/output device 140.

Figure 5:
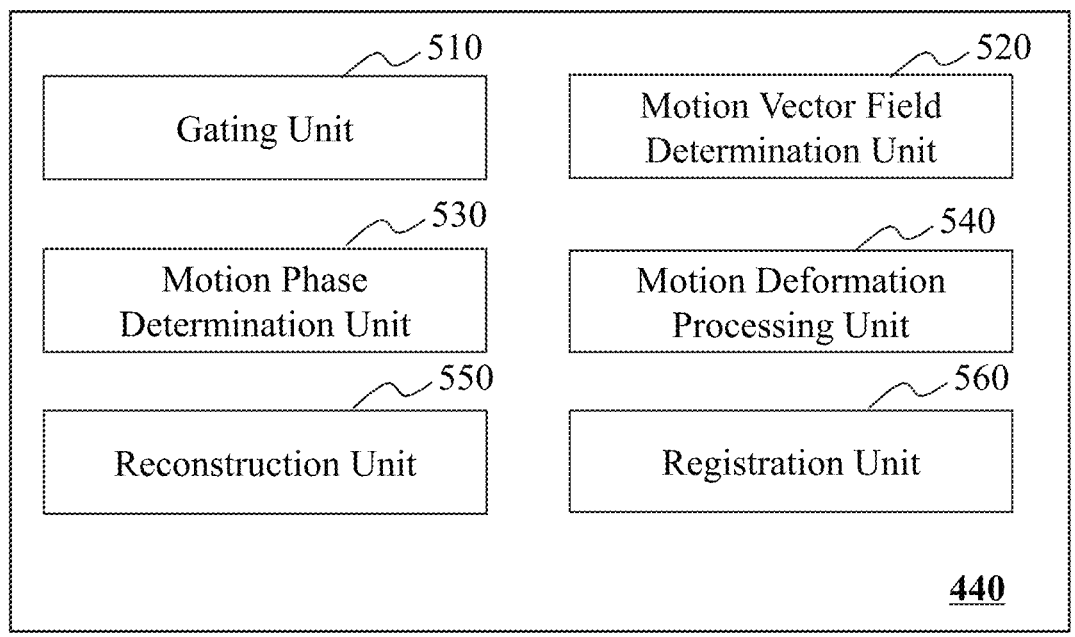
FIG. 5 is a block diagram illustrating an exemplary processing module according to some embodiments of the present disclosure.

FIG. 5 is a block diagram illustrating an exemplary processing module 440 according to some embodiments of the present disclosure. As shown in FIG. 5, the processing module 440 may include a gating unit 510, a motion phase determination unit 530, a motion vector field determination unit 520, a reconstruction unit 550, a motion deformation processing unit 540, and a registration unit 560. In some embodiments, the processing module 440 may be implemented by CPU 230 in the computing device 200, CPU 340 in the mobile device 300, or any component in the imaging system 100. At least a portion of the processing module 440 may be implemented on a computing device as illustrated in FIG. 2 or a mobile device as illustrated in FIG. 3. A module may be a hardware circuit that is designed to perform one or more of the following actions, a set of instructions stored in one or more storage media, and/or any combination of the hardware circuit and the one or more storage media.

The gating unit 510 may gate PET data into a plurality of groups of gated PET data. The PET data may be the projection data of a PET scanning. A group of gated PET data may be used to reconstruct a plurality of gated PET images. The gating of the PET data may be performed by dividing the PET data into a plurality of groups or frames based on a time interval associated with a motion. The time interval may be determined based on the amplitudes of the motion, and/or the variation of the amplitudes with time.

For example, in a respiratory cycle, from an end-expiration to an end-inspiration, the motion amplitude may increase from a lowest value to a highest value. An average value of the lowest value and the highest value may be determined to be a midway amplitude. In this case, a first time interval may be determined to be the time period between the time point corresponding to an end-expiration and the time point corresponding to the midway amplitude that first appears during the respiration motion after the end-expiration. A second time interval may be determined to be the time period between the time point corresponding to the timing of the midway amplitude and the time point corresponding to the end-inspiration that first appears during the respiration motion after the midway amplitude. Similarly, the number of groups may vary if there are more midway amplitudes. In some embodiments, the time interval may be determined based on a predetermined value. For example, the predetermined value may be a constant. The PET data may be transmitted or stored in an electronic data form. The electronic data form may include a digital imaging and communications in medicine (DICOM) data form, a Mosaic data form, an Analyze data form, a neuroimaging informatics technology initiative (NIfTI) data form, or the like, or any combination thereof. For example, the PET data may be stored in the storage module 420 in the DICOM data form.

The PET images and/or the PET data may be obtained from the acquisition module 410, or any other components in the imaging system 100. For example, the PET data may be generated by scanning a thorax of a patient using the imaging system 100 (e.g., a PET imaging system). In some embodiments, the PET data may be transmitted or received in the form of an electronic signal. The electronic signal may be used to encode the PET data. Merely by way of example, the PET data may be obtained from a cloud storage (e.g., a public cloud) via the network 160. In some embodiments, the PET data may be reconstructed to a plurality of PET images.

In some embodiments, the PET images and/or the PET data may correspond to CT data, or at least one CT image. For instance, the PET images and/or the PET data, and the CT data and/or CT image(s) may be obtained by scanning a same area of a same subject (for example, a patient). The CT data may be obtained by scanning a patient before or after a PET scanning of the patient. For example, the CT data may be acquired by scanning a patient who remains still. After the CT scanning, the PET data may be acquired by scanning the patient at (essentially) the same patient position. As another example, the CT image or CT data may be obtained after a PET scanning of the patient.

In some embodiments, the PET data and/or the corresponding CT data may be processed. For example, the PET data and/or the corresponding CT data may be used to reconstruct a plurality of PET images and/or a plurality of CT images. The plurality of CT images may be CT images in a transverse plane, a coronal plane, or a sagittal plane. The transverse plane, the coronal plane, and the sagittal plane are used in the medical field and are perpendicular to each other. For example, the CT images may include a plurality of 2D images in a transverse plane. In some embodiments, the corresponding CT data may be processed for an attenuation correction of a corresponding PET image reconstruction. Description regarding attenuation correction of a PET image reconstruction may be found elsewhere in the present disclosure. See, for example, FIG. 6A and the description thereof.

The PET data may be gated or divided based on a gating condition. For instance, according to the gating condition, the PET data may be divided into a plurality of groups of gated PET data. In some embodiments, the gating condition may be associated with a type of motion of the subject (or referred to as a subject motion). The subject motion may include a respiratory motion (or referred to as a respiration motion) with a plurality of respiratory phases (related description may be found elsewhere in the present disclosure), a cardiac motion with a plurality of cardiac phases, a gastrointestinal motion with a plurality of gastrointestinal phases, a skeletal muscle motion with a plurality of skeletal muscle motion phases, or the like, or any combination thereof. For example, the subject (e.g., a patient) may undergo respiratory motion during a PET scanning and/or a CT scanning. The methods and systems are described with reference to a respiratory motion for illustrated purposes, and not intended to limit the scope of the present disclosure. The systems and methods disclosed herein may be applied in the context of other motion types including, for example, cardiac motion, gastrointestinal motion, skeletal muscle motion, etc., or a combination thereof.

The gating condition may include a gating parameter, a time interval, a region of interest, a compression algorithm, or the like, or any combination thereof. The gating parameter may include a respiratory phase, a cardiac phase, a gastrointestinal phase, a skeletal muscle motion phase, or the like, or any combination thereof. The respiratory phase may correspond to respiratory motion of the subject (e.g., the patient). The respiratory motion of the subject may include an inhaling phase (or referred to as an inspiratory phase) and/or an exhaling phase (or referred to as an expiratory phase). For example, in the inhaling phase, the patient may expand his/her chest to cause a negative pressure in the chest. The negative pressure may cause the air to flow into the lungs of the patient. As another example, in the exhaling phase, the patient may shrink the chest to cause a positive pressure in the chest. The positive pressure may press the air out of the lungs.

In some embodiments, the gating unit 510 may divide the PET data based on the motion information acquired using the gating system 180. The gating system may include a device for detecting a motion of the subject, a control panel, a marker fixed on surface of the subject for indicating motion of the subject, or the like, or any combination thereof. In some embodiments, the gating system may include a motion detection device such as, for example, a gating camera, a belt secured around the chest of the subject or another pressure measurement technique or device to measure the change of pressure during the breathing of the subject. In some embodiments, the gating camera may be an infrared camera. The gating system 180 may be used to collect information relating to, for example, respiration, heartbeat, etc. The gating system 180 may analyze the information to obtain the gating parameter (e.g., the respiratory phase). In some embodiments, motion information may be derived from the imaging data including, for example, PET data. Exemplary gating techniques, including self-gating, may be found in, for example, U.S. application Ser. No. 15/386,048 filed Dec. 21, 2016 and Ser. No. 15/618,425 filed Jun. 9, 2017, both entitled "METHODS AND SYSTEMS FOR EMISSION COMPUTED TOMOGRAPHY IMAGE RECONSTRUCTION," the contents of which are hereby incorporated by reference.

In some embodiments, the gated PET image may be the PET image associated with a gating parameter (e.g., a respiratory phase). For example, the gated PET image may include a first PET image corresponding to a first group of PET data and a second PET image corresponding to a second group of PET data. The first group of PET data may correspond to a first respiratory phase (e.g., the inhaling phase of the patient), and the second group of PET data may correspond to a second respiratory phase (e.g., the exhaling phase of the patient). A first gated PET image reconstructed using the first group of PET data may correspond to the first respiratory phase. A second gated PET image reconstructed using the second group of PET data may correspond to the second respiratory phase. The gated PET images may be gated 3D PET images. More details of the operation of gating the PET data may be found elsewhere in the present disclosure. See, for example, description regarding operation 630 in FIG. 6A or process 700 in FIG. 7. The gated PET image may be further processed in the motion vector field determination unit 520.

The motion vector field determination unit 520 may determine a motion vector field based on the gated PET images. In some embodiments, the motion vector field may include a plurality of motion vectors. A motion vector may be used to describe the motion of a spatial point of the subject between the motion phases corresponding to the two gated PET images. In some embodiments, a motion vector may be determined by registering the two gated PET images. For example, after registering the two gated PET images, locations of two voxels in the gated PET images corresponding to a same spatial point of the subject may be determined. Then the motion vector field determination unit 520 may determine the corresponding motion vector of the spatial point based on the locations of the corresponding two voxels. A motion vector field may be a set including a portion or all of the motion vectors between two gated PET images. The motion vector field may be used to describe a motion relationship of spatial points between two motion phases corresponding to the two gated PET images.

In some embodiments, a motion vector field may be determined based on two gated PET images corresponding to two different respiratory phases (e.g., a first respiratory phase, and a second respiratory phase different from the first respiratory phase). In some embodiments, a motion vector field may be determined based on two sequential gated PET images that correspond to two sequential respiratory phases among the respiratory phases whose PET data are acquired. For example, the motion vector field determination unit 520 may determine a motion vector field corresponding to an Nth gated PET image and an (N+1)th gated PET image.

In some embodiments, the motion vector field determination unit 520 may determine a motion vector field based on the registration of each of the gated PET images with a reference image. The reference image may be determined by selecting one gated PET image from the plurality of gated PET images based on a selection condition (e.g., a sequence of the image). The gated PET images may be 3D PET images. For example, a first gated PET image may be selected as the reference image. The other gated PET images may be registered with the first gated PET image. The registration may be performed by the registration unit 560.

The motion phase determination unit 530 may determine a similarity between a CT image and a plurality of gated PET images to determine the respiratory phase of the CT image.

The similarities between a CT image and the gated PET images may be used to determine whether the CT image is the same as or similar to one of gated PET images in terms of a motion phase. Exemplary operations for assessing the similarity of a CT image and a gated PET image may be found elsewhere in the present disclosure. See, for example, 660 in FIGS. 6A and 810 in FIG. 8, and the description thereof. In some embodiments, the similarity may include a pixel-based similarity, a voxel-based similarity, an entropy-based similarity, a mutual information similarity, or the like, or any combination thereof. The pixel-based similarity may be determined by comparing at least one of pixels between the CT image and the PET image. The voxel-based similarity may be determined by comparing at least one of voxels between the CT image (e.g., a 3D CT image) and the PET image (e.g., a 3D PET image). The entropy-based similarity may be determined by comparing information gain between the CT image and the PET image. The mutual information similarity may be determined by comparing mutual information between the CT image and the PET image.

The similarity may be presented as a number, a percentage, a value, a text, a matrix, a determinant, or the like, or any combination thereof. For example, the similarity may be expressed as 2, 4, 5, 30, or any integer. In some embodiments, one or more similarities may be ranked. For example, the one or more similarities may be ranked from the minimum to the maximum. As another example, the motion phase determination unit 530 may analyze the similarities of a CT image with respect to the plurality of gated PET images, and identify the maximum similarity based on the analysis. The CT image and the gated PET image with the maximum similarity with the CT image may be considered corresponding to the same or the most similar motion phase with the CT image.

In some embodiments, for a CT image, the motion phase determination unit 530 may further determine a motion phase of the CT image based on the similarities between the CT image and the gated PET images. The motion phase of the CT image may correspond to the subject motion such as the respiratory motion with a plurality of respiratory phases, the cardiac motion with a plurality of cardiac phases, the gastrointestinal motion with a plurality of gastrointestinal phases, a skeletal muscle motion with a plurality of skeletal muscle motion phases, etc. For example, the phase of the CT image may be the respiratory phase of the CT image. The CT image may be determined to correspond to the motion phase (e.g., the respiratory phase) of the gated PET image with the maximum similarity among the gated PET images. For each of the plurality of CT images, the respective motion phase of the CT image may be so determined.

The motion deformation processing unit 540 may deform a CT image. The motion deformation processing unit 540 may process the CT image by determining a deformation vector field based on the similarities and the corresponding motion vector fields with respect to the plurality of gated PET images. For example, the deformation processing unit 540 may determine a gated PET image achieving the maximum similarity with the CT image, and determining the motion vector field of the gated PET image with respect to the reference image as the corresponding motion vector field. In some embodiments, the motion deformation processing unit 540 may process the CT image based on the deformation vector to generate a corrected CT image. For example, the motion deformation processing unit 540 may deform the CT image with a first respiratory phase of the PET image into a corrected CT image with a second respiratory phase. Description regarding the deformation of a CT image to generate a corrected CT image may be found elsewhere in the present disclosure. See, for example, 680 in FIG. 6A or the process 900 in FIG. 9, and the description thereof.

The reconstruction unit 550 may reconstruct a PET image based on the corrected CT images and the PET data. In some embodiments, the PET image may integrate information of the PET data and the corrected CT images. In some embodiments, the anatomical information of the subject may be obtained from the corrected CT images. In some embodiments, the reconstructed PET image may exhibit functional information such as a metabolic intensity of a tumor, etc. The functional information may be obtained from the PET data. For example, the reconstructed PET image may show a tumor with a high metabolic intensity located in a liver region, while a corrected CT image corresponding to the reconstructed PET image may show a more precise location or contour of the tumor.

The corrected CT images may be used to generate an attenuation map including a plurality of attenuation coefficients by the reconstruction unit 550. The attenuation map may be used to correct the PET data. The PET data and the attenuation map may be used to reconstruct a PET image by the reconstruction unit 550.

The registration unit 560 may register the gated PET images. In some embodiments, the registration unit 560 may register the gated PET images with a reference PET image. The reference PET image may be one of the gated 3D PET images. Any one of the gated 3D PET images may be designated as the reference PET image, or referred to as the reference gated 3D PET image. The registration may be implemented based on at least one registration algorithm. Exemplary registration algorithms may include a point-based registration algorithm (e.g., an anatomic-landmark-based registration algorithm), a curve-based registration algorithm, a surface-based registration algorithm (e.g., an surface-profile-based surface profile), a spatial alignment registration algorithm, a cross-correlation registration algorithm, a mutual-information-based registration algorithm, a sequential similarity detection algorithm (SSDA), a nonlinear transformation registration algorithm, an optical flow, demons registration algorithm, B-spline registration algorithm, or the like, or any combination thereof.

In some embodiments, the registration may be performed based on rigid transformation, an affine transformation, a projection transformation, a nonlinear transformation, an optical-flow-based registration, a similarity measurement, or the like, or any combination thereof. The similarity measurement may include a mutual-information-based measurement, a Fourier-analysis-based measurement, or the like, or any combination thereof. Merely by way of example, the registration unit 560 may use the optical flow algorithm to register the gated PET images, and generate motion vector fields for the plurality of gated PET images.

The gating unit 510, the motion vector field determination unit 520, the motion phase determination unit 530, the motion deformation processing unit 540, the reconstruction unit 550, and the registration unit 560 in the processing module 440 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a Zig-Bee, a Near Field Communication (NFC), or the like, or any combination thereof. In some embodiments, any two of the modules may be combined as a single module, and any one of the modules may be divided into two or more units.

FIG. 6A is a flowchart illustrating an exemplary process 600 for reconstructing a PET image according to some embodiments of the present disclosure. At least a portion of the process 600 may be implemented on a computing device as illustrated in FIG. 2 or a mobile device as illustrated in FIG. 3. In some embodiments, one or more operations of process 600 for reconstructing a PET image may be implemented in the image processing system 100 illustrated in FIG. 1. For example, the process 600 may be stored in the storage module 420 of the data processing system 130 in the form of instructions, and invoked and/or executed by the data processing system 130 (e.g., the processor 230 of the data processing system 130).

In 610, the acquisition module 410 may obtain a plurality of CT images corresponding to a scanning area of a subject. The plurality of CT images may be 2D images, and may also refer to CT image layers (e.g., slice images) of a 3D CT image. The CT image layers may correspond to a portion of the 3D CT image. For instance, the 3D CT image includes ten CT image layers, and some or all of the ten CT image layers are processed according to process 600. In some embodiments, the plurality of CT images may also include processed CT images (e.g., one or more attenuation maps relating to the CT images). The plurality of CT images may be generated by a CT scanner, or transmitted from a storage device via the network 160. The scanning area may include a brain, a lung, a liver, a kidney, a bone, any organ or region of interest (ROI) associated with a subject (e.g., a patient). In some embodiments, the scanning area may include a whole body. The subject (e.g., a patient) may need to keep still or maintain his/her position during the scanning. For example, if the scanning area is the spine of the patient, the patient may lie on the abdomen on the table 114 and keep the same patient position for a few minutes (e.g., about 3 minutes, about 5 minutes, about 10 minutes, about 15 minutes, etc.), and during the scanning the patient may breathe normally.

In some embodiments, the subject may include a patient, an animal, a phantom, or a portion thereof including, for example, an artificial limb, an artificial heart, a tumor, any structure or organ that may be examined using X rays, or the like, or any combination thereof.

In the CT/PET system, the imaging device 110 may scan a patient. The projection scanning may use a $^{68}$Ge generator to emit $^{68}$Ge ray. In some embodiments, the projection scanning may use X rays to scan the patient, and obtain the plurality of CT images. The plurality of CT images may be used to correct PET images corresponding to the same Region of Interest (ROI) as the CT images. The CT images used to correct PET images may have a high image resolution, e.g., an image resolution of 0.5 mm.

In 620, the acquisition module 410 may also obtain PET data corresponding to the same scanning area of the subject. The PET data may correspond to the scanning area of the CT scanning of the subject described in connection with 610. For example, if a CT scanning of a chest of the patient is performed, the PET scanning of the chest of the patient may be performed when the patient keeps essentially the same patient position, in order to facilitate the combination of information of the PET data and the CT data together. The patient may breathe normally during the PET scanning. In some embodiments, the PET data may correspond to different respiratory phases. For example, a first frame of PET data may correspond to one respiratory phase (e.g., the inhaling phase), and a second frame of PET data may correspond to another respiratory phase (e.g., the exhaling phase).

In some embodiments, the speed of CT scanning may be about 1.5 seconds/table position. The speed of the PET scanning may be about 5 minutes/table position. If the patient undergoes respiratory motion, the acquired CT images or PET images may include motion artifacts. The respiratory motion of the subject may include an inhaling phase and/or an exhaling phase. In some embodiments, the respiratory motion of the patient may lead to that a shift (or referred to as mismatch) of the location of a same portion (e.g., an organ, a tissue, etc.) of the subject in a (2D or 3D) CT image with respect to a corresponding gated (2D or 3D) PET image. A 2D CT image may also be referred to as a CT image layer. A 2D PET image may also be referred to as a PET image layer. For example, the location of the liver may be different in the 3D CT image than that in the gated PET image. For example, a plane of the lung (e.g., Oxy or a transverse plane, etc.) may correspond to one 2D CT image layer and one gated 2D PET image layer, the 2D CT image layer may be generated corresponding at an inhaling phase of the respiratory motion, while the gated 2D PET image layer may be obtained during an exhaling phase of the respiratory motion, and the outer edge of a lung in the plane Oxy may show a shift or mismatch between the CT image and the gated PET image layer. For instance, such a shift or mismatch may be observed by comparing a PET image layer in coronal or sagittal plane of a 3D PET image reconstructed from on gated PET data with that of a 3D CT image.

Merely by way of example, a 3D CT image is used in the reconstruction of a gated PET image. A point of a lung of the subject in the 3D CT image does not match the same point of lung in the gated PET image due to the shift. The 3D PET image reconstructed directly based on the 3D CT image may show low image quality, if the attenuation map generated based on the 3D CT image is used for reconstructing the 3D PET image.

In 630, the gating unit 510 may gate the PET data with respect to different respiratory phases of the subject. The gated PET data may be used to reconstruct one or more gated PET images. The reconstruction may be performed by the reconstruction unit 550 described elsewhere in the present disclosure. The gated PET data may include information associated with a respiratory signal of the respiratory motion. In some embodiments, the gating unit 510 may obtain information of a respiratory signal relating to a respiratory motion from the PET data, and determine the respiratory signal of the respiratory motion.

In some embodiments, the respiration signal may be a signal acquired from a source other than the PET data. For instance, the external signal may be determined from the gating system 180. The gating system 180 may collect information relating to, for example, breathing, heartbeat, etc. The gating system 180 may analyze the information to obtain the respiration signal. The gating system 180 may include a device for detecting motion of the subject, a control panel, a marker fixed on surface of the subject for indicating motion of the subject, or the like, or any combination thereof. In some embodiments, the gating system may include a motion detection device, such as, for example, a gating camera, or a belt secured around the chest of the subject or another pressure measurement technique or device to measure the change of pressure during the breathing of the subject. In some embodiments, the gating camera may be an infrared camera. For example, if the imaging device 110 is scanning the patient, the gating system may be triggered automatically. The gating system may collect information associated with respiration motion. The data collected by the gating system may be stored together with the PET data or CT data.

In some embodiments, the respiratory signal may be approximated by a sine function, a cosine function, a polynomial function, a pulse function, or the like, or any combination thereof. In some embodiments, the respiratory signal may be expressed in a two-dimensional coordinate. The two-dimensional coordinate may include a first coordinate axis (or the X axis) representing time, and a second coordinate axis (or the Y axis) representing amplitude or value. For example, the respiration signal may be approximated by a sine function in the two-dimensional coordinate. The respiration signal may show the amplitude in the Y axis, and the amplitude may vary depending on the time in the X axis. In some embodiments, the respiration signal may be approximated by the sine signal or the cosine signal. The gating unit 510 may approximate the respiration signal using, for example, the sine function, the cosine function, etc. For example, the respiration signal may be approximated by the formula (1):

$$Y = c * \sin(aX + b), \quad (1)$$

where Y is the amplitude of the respiratory motion, X is the time of the respiratory motion, and a, b, and c are constant parameters.

In some embodiments, the respiratory signal may be divided into a plurality of respiratory phases. In some embodiments, the respiratory signal may be determined or divided into N respiratory phases, where N may be an integer greater than 1. For example, the gating unit 510 may divide the respiratory signal into 4 respiratory phases, each of which may correspond to a different part in a cycle of the respiratory signal. In some embodiments, the gating unit 510 may divide the respiratory signal into a fixed number of the respiratory phases automatically. In some embodiments, the gating unit 510 may divide the respiratory phase into N respiratory phases according to the instruction of a user (e.g., a doctor). For example, a user (e.g., a doctor or a radiologic technologist) may divide the respiratory signal into 3 respiratory phases based on his/her clinical experiences. The user may provide his/her instruction via a user interface implemented on, e.g., a mobile device as illustrated in FIG. 3.

In some embodiments, the respiratory signal may be divided according to an amplitude of the respiratory signal. For example, a cycle of the respiratory signal may be divided based on the amplitude of the respiratory signal. If the amplitude of the respiratory signal is segmented to n parts (e.g., from the maximum amplitude to the minimum amplitude), the n parts of the respiratory signal may correspond to n respiratory phases. In some embodiments, the respiratory signal may be divided, based on the time of the respiratory signal, into N parts, and the N parts may correspond to N respiratory phases. For example, if a cycle of the respiratory signal ranges from 0 second to 5 seconds, a cycle of the respiratory signal may be divided according to a time interval (e.g., 0.5 seconds, or 1 seconds), and this cycle of the respiratory signal may be divided into N respiratory phases (e.g., 5/0.5 or 10 respiratory phases, 5/1 or 5 respiratory phases). Exemplary gating techniques, including self-gating, may be found in, for example, U.S. application Ser. No. 15/386,048 filed Dec. 21, 2016 and Ser. No. 15/618,425 filed Jun. 9, 2017, both entitled "METHODS AND SYSTEMS FOR EMISSION COMPUTED TOMOGRAPHY IMAGE RECONSTRUCTION," the contents of which are hereby incorporated by reference.

In some embodiments, the gating unit 510 may determine a plurality of gated PET images based on the respiratory phases. In some embodiments, the gated PET images may be reconstructed based on the gated PET data. In some embodiments, the gated PET images may be determined based on the respiratory phases. For example, if the respiratory signal is divided into 4 respiratory phases, the gating unit 510 may determine 4 groups of gated PET data, and the 4 gated PET images may be reconstructed based on the 4 groups of gated PET data. In some embodiments, a series of gated PET images may be reconstructed based on a group of gated PET data. For example, if a cycle of respiratory motion is divided into 4 respiratory phases corresponding to 4 time intervals, the PET data that may include data corresponding to multiple respiratory cycles may be gated to provide several groups (or referred to as frames) of gated PET data corresponding to the 4 time intervals; a series of gated PET images (e.g., 4 gated PET images) may be obtained by way of reconstruction of groups (or frames) of gated PET data.

In 640, the registration unit 560 may register the gated PET images. In 640, the registration unit 560 may register the gated PET images based on at least one registration algorithm. Exemplary registration algorithms may include a point-based registration algorithm (e.g., an anatomic-landmark-based registration algorithm), a curve-based registration algorithm, a surface-based registration algorithm (e.g., an surface-profile-based surface profile), a spatial alignment registration algorithm, a cross-correlation registration algorithm, a mutual-information-based registration algorithm, a sequential similarity detection algorithm (SSDA), a nonlinear transformation registration algorithm, an optical flow, or the like, or any combination thereof. In some embodiments, the registration executed in 640 may include an automatic registration, a semi-automatic registration, or an artificial registration. In some embodiments, the registration may be performed based on rigid transformation, an affine transformation, a projection transformation, a nonlinear transformation, an optical-flow-based registration, a similarity measurement, or the like, or any combination thereof.

Merely by way of example, the optical flow may include a sparse optical flow and a dense optical flow. The sparse optical flow may focus on a sparse point in a PET image. For instance, a corner point may be used as a sparse point. In some embodiments, the dense optical flow may focus on the offset of pixels or voxels in the PET image. In some embodiments, the optical flow may further include a Lucas-Kanade algorithm, a Horn-Schunck algorithm, a Buxton-Buxton algorithm, a general variational algorithm, a block-based algorithm, a discrete optimization algorithm, or the like, or any combination thereof.

In some embodiments, the registration unit 560 may register each of the gated PET images against a same reference image. The reference image may be selected from the plurality of gated PET images. For example, the first gated PET image may be designated as the reference image, and each of the gated PET images may be registered with the first gated PET image. As another example, the last gated PET images may be designated as the reference images, and each of the gated PET images may be registered with the last gated PET image.

In 650, the motion vector field determination unit 520 may determine a motion vector field based on the registration. The motion vector field may include a plurality of motion vectors. A motion vector may be used to describe a motion of a spatial point of the subject between the motion phases corresponding to the two gated PET images. For example, in 640 the motion vector field determination unit 520 may determine a first location of a point in the Nth PET image to be (X1, Y1, Z1), and a second location of the point in the (N+1)th PET image to be (X2,Y2, Z2). The motion vector field determination unit 520 may further determine a motion vector to be (Ux, Uy, Uz) based on the first location and the second location of the point, where Ux may be equal to (X1−X2), Uy may be equal to (Y1−Y2), and Uz may be equal to (Z1−Z2).

In some embodiments, a spatial point corresponding to different respiratory phases may be represented as (x, y, z, t), where the x, y, and z represent values in the X axis, the Y axis, and the Z axis, respectively, and the t represents the respiratory phase for a PET image having a voxel corresponding to the spatial point. In some embodiments, the motion vector at the spatial point of (x,y,z) in a respiratory phase of t may be represented as a coordinate $(m_u(x,y,z,t), m_v(x,y,z,t), m_w(x,y,z,t))$, where $m_u$ represents a motion vector component in the x axis direction, $m_v$ represents a motion vector component in the y axis direction, $m_w$ represents a motion vector component in the z axis direction. For example, if a motion vector corresponds to a spatial point (3,5,7) and a respiratory phase numbered as 1, and a reference respiratory phase numbered as 0, the motion vector may be expressed as $(m_u(3,5,7,1), m_v(3,5,6,1), m_w(3,5,7,1))$, representing a movement of the spatial point (3,5,7) from the reference respiratory phase 0 to the respiratory phase 1.

In 660, the motion phase determination unit 530 may determine the respiratory phase of the CT image (also referred to as a CT image layer of a 3D CT image). In some embodiments, the determination may be based on a relationship between the gated PET images and the CT image. A gated 3D PET image may include a plurality of gated PET image layers corresponding to a same respiratory phase of a respiratory motion of a subject. A CT image layer of the 3D CT image and a gated PET image layer may correspond to a same group of spatial points relating to the subject. A group of spatial points relating to the subject may include spatial points within or on the surface of the subject, or in the vicinity of the subject when the subject is scanned to provide CT image data (corresponding to the 3D CT image, the CT image layers, etc.), or PET image data (corresponding to the 3D PET images, the gated 3D PET images, the gated PET image layers of a gated 3D PET image, etc.) that are analyzed or processed as described herein.

The relationship between the gated PET images and the CT image layer may be assessed in terms of the similarities between a plurality of gated PET image layers and the CT image layer corresponding to a same group of spatial points relating to the subject. The plurality of gated PET image layers, one from each of a plurality of gated 3D PET images, may correspond to different respiratory phases of a respiratory motion of the subject during an image scan. In some embodiments, the similarity between the CT image layer and a gated PET image layer may be determined. For example, one CT image layer may be compared with three gated PET image layers (e.g., a first gated PET image layer, a second gated PET image layer, and a third gated PET image layer) corresponding to three gated 3D PET images corresponding to respiratory phases different from each other, and three similarities may be determined. The three similarities may include a first similarity between the CT image layer and the first gated PET image layer, a second similarity between the CT image layer and the second gated PET image layer, and a third similarity between the CT image layer and the third gated PET image layer.

In some embodiments, the similarity may include a pixel-based similarity, an entropy-based similarity, a mutual information similarity, a contour-based similarity, or the like, or any combination thereof. The pixel-based similarity may be determined by comparing the CT image layer and a gated PET image layer at the pixel level. A pixel from the CT image layer may be compared with a corresponding pixel in the gated PET image layer. As used herein, two pixels in two different images (e.g., a CT image layer and a PET image layer, two CT image layers, two PET image layers, etc.) are considered to correspond to each other if they both correspond to a same spatial point. The entropy-based similarity may be determined by comparing information gain between the CT image layer and the gated PET image layer. The mutual information similarity may be determined by comparing mutual information between the CT image layer and the gated PET image layer. The contour-based similarity may be determined by comparing a contour of an organ in the CT image layer and the corresponding gated PET image layer. The CT image layer and the gated PET image layer may be preprocessed respectively to extract the contour of the organ.

A similarity may be presented as a number, a percentage, a value, a text, a matrix, a determinant, or the like, or any combination thereof. For example, a similarity may be expressed as 2, 4, 5, 30, or any integer. In some embodiments, one or more similarities may be ranked. For example, the one or more similarities of a CT image layer with respect to a plurality of gated PET image layers may be ranked from the minimum to the maximum, or vice versa. As another example, the motion phase determination unit 530 may analyze the similarities, and select the maximum similarity. The maximum similarity may indicate that the gated PET image layer is the same as or the most similar to the CT image layer in terms of the motion phase. For example, the gated PET image layer with the second respiratory phase may show the maximum similarity with the CT image layer, indicating that this gated PET image layer is the same as or the most similar to the CT image layer in terms of the respiratory phase.

In some embodiments, the motion phase determination unit 530 may further determine the motion phase of the CT image layer based on the similarities between the CT image layer and the gated PET image layers. The motion phase of the CT image layer may correspond to the subject motion such as the respiratory motion with a plurality of respiratory phases, the cardiac motion with a plurality of cardiac phases, the gastrointestinal motion with a plurality of gastrointestinal phases, a skeletal muscle motion with a plurality of skeletal muscle motion phases. For example, a CT image layer may correspond to a respiratory phase. In some embodiments, a total number of respiratory phases of the CT image layers may be the same as or fewer than the number of respiratory phases of the gated PET image layers. If the scanning speed of a CT scanner is higher than the breathing speed of the patient, one or more CT image layers may correspond to a same motion phase as determined according to the process 800.

In some embodiments, the determination of the respiratory phase of the CT image layer may be based on another respiratory signal obtained by the gating system 180 during both PET and CT scanning. For example, during the CT scanning that provides the 3D CT image, the gating system 180 may obtain the respiratory motion of the subject, and designate one of the respiratory phases of the gated PET images for each of the CT image layers. Respiratory phases of respiratory motion may correspond to an amplitude range of the respiratory motion. Such an amplitude range of respiratory motion may be reflected in a respiratory signal recorded during a CT or PET scan. For example, the respiratory phases of the gated PET images are determined based on the amplitude range of the respiratory motion of the subject. The gating system 180 may designate a respiratory phase of a CT image layer based on the amplitude of respiratory signal acquired at the time of the CT scanning. The correspondence between an amplitude and a respiratory phase applied in this motion phase analysis of a CT image layer may be the same as the correspondence between an amplitude and a respiratory phase applied in the gating of the PET data and/or the designation of the respiratory phases of the gated PET images based on a respiratory signal.

In some embodiments, after the respiratory phases of the CT image layers are determined, a respiratory phase curve may be determined. The respiratory phase curve may locate in a coordinate system with a horizontal axis representing the layer numbers of the CT image layers, and a vertical axis representing the respiratory phases of the CT image layers. The respiratory phase curve may relate to the axial coordinate of the helical CT scanning that provides the 3D CT image. In some embodiments, the processing module 440 may perform analysis and/or filtering with respect to the respiratory phase curve to reduce noises in the matching of the CT image layer and the gated PET image layer.

In 670, the motion deformation processing unit 540 may correct CT image layers to generate corrected CT image layers. The corrected CT image layers may be used to form a corrected 3D CT image and further used to reconstruct a 3D PET image that may show information of the corrected CT image layers and the PET data. A corrected CT image layer may be a processed CT image layer that corresponds to a certain respiratory phase (e.g., a reference respiratory phase). The correction may remove or reduce a difference between the processed CT image layers that are due at least partially to that the corresponding CT image layers relate to different respiratory phases. The motion deformation processing unit 540 may generate corrected CT image layers (or corrected 3D CT image) that correspond to a same respiratory phase as each other.

For instance, for a 3D CT image including a plurality of CT image layers, a CT image layer corresponds to a respiratory phase. At least two of the CT image layers of the 3D CT image correspond to two different respiratory phases. For a 3D CT image obtained by way of a CT scan, a respiratory phase of some CT image layers may be designated as a reference respiratory phase (corresponding to a reference frame of a gated 3D PET image), and other CT image layers of the 3D CT image may be corrected with respect to the reference respiratory phase, and the corrected CT image layers may constitute a corrected 3D CT image corresponding to the reference respiratory phase. Based on the same 3D CT image, if a different respiratory phase is designated as the reference respiratory phase, the CT image layers of the 3D CT image may be corrected and a corrected 3D CT image corresponding this reference respiratory phase may be generated. Accordingly, corrected 3D CT images with respect to different respiratory phases may be generated based on the same 3D CT image obtained in one CT scan. Such corrected 3D CT images corresponding to different respiratory phases may be applied in the reconstruction of gated 3D PET images corresponding to different respiratory phases.

In some embodiments, the motion deformation processing unit 540 may generate a corrected CT image layer based on a deformation vector field including a plurality of deformation vectors. A deformation vector may be a 2D vector, 3D vector, or an N-dimensional vector. For example, the motion deformation processing unit 540 may deform the CT image layer corresponding to a first respiratory phase into a corrected CT image layer corresponding to a second respiratory phase.

In some embodiments, a deformation vector field may be determined based on a motion vector field. A deformation vector field may correspond to a motion vector field. For example, the deformation vector field for a CT image layer from its designated respiratory phase N to a reference respiratory phase may be determined based on the motion vector field for the PET image layer of gated 3D PET image at the same phase. The motion vector field for the PET image layer of the Nth gated 3D PET image may be with respect to a reference gated PET image layer of a reference PET image (e.g., the first gated PET image). The CT image layer of phase N, the gated PET image layer of the same phase, and the reference gated PET image layer may correspond to a same group of spatial points. Details about the determination of the deformation vector field based on the motion vector field may be found elsewhere in the present disclosure. See, for example, the description regarding 910 in FIG. 9.

In 680, the reconstruction unit 550 may reconstruct a PET image based on the corrected CT image layers and the PET data. In some embodiments, the reconstruction unit 550 may use a reconstruction algorithm to generate the PET image. The reconstruction algorithm may include an iterative reconstruction algorithm (e.g., a statistical reconstruction algorithm), a Fourier slice theorem algorithm, a filtered back projection (FBP) algorithm, a compressed sensing (CS) algorithm, a fan-beam reconstruction algorithm, a maximum likelihood expectation maximization (MLEM) algorithm, an ordered subset expectation maximization (OSEM) algorithm, a maximum a posterior (MAP) algorithm, an analytic reconstruction algorithm, or the like, or any combination thereof.

In some embodiments, a corrected CT image may be superimposed with a gated PET image so that the corrected CT image may provide structural information in combination with the functional information provided by the gated PET image.

In some embodiments, the reconstruction may further be based on the corrected CT image layers for attenuation correction. The corrected CT image layers may be used to generate an attenuation map applied in the PET image reconstruction. The reconstructed PET image may be a gated PET image with the reference respiratory phase if the CT image layers are corrected to provide corrected CT image layers corresponding to the reference respiratory phase. In some embodiments, the reconstructed PET image may be a gated PET image with any of the respiratory phases considering that any one of the respiratory phases may be designated as the reference respiratory phase. By way of the attenuation correction, attenuation artifacts in the PET image may be decreased. The attenuation artifacts in the PET image may be caused by attenuation of photon rays (e.g., γ rays) when they pass through the subject (e.g., a patient). For example, a positron emitted by an imaging agent taken by a patient encountering an electron from a tissue of the patient may annihilate. A pair of gamma photons may be generated in response to the annihilation. When the photons pass through the tissue to reach the detector 112 (e.g., a PET detector), at least a portion of the photons may reach the detector 112, and the rest of the photons may be scattered or absorbed by the tissue of the patient. The photons scattered or absorbed may cause the attenuation of the photon ray which in turn may contribute to the attenuation artifacts in the PET image.

In some embodiments, the attenuation artifacts may be corrected by way of the attenuation correction that may include the application of at least one of attenuation coefficient. Merely by way of example, the attenuation coefficient may be a tissue attenuation coefficient corresponding to the γ ray in an energy level of 511 KeV. The tissue attenuation coefficient may be used to determine an attenuation correction factor of the γ ray. For instance, the attenuation correction factor may be determined by formula (2):

$$ACF = e^{\int u(x)dx}, \qquad (2)$$

where ACF represents the attenuation correction factor of the γ ray, and u represents the tissue attenuation coefficient.

In some embodiments, the attenuation correction factor may be determined according to the corrected CT image layers. For example, a tissue attenuation coefficient corresponding to the X ray may be determined based on the corrected CT image layer. The tissue attenuation coefficient corresponding to the X ray may be transformed into the tissue attenuation coefficient corresponding to the γ ray, and the tissue attenuation coefficient corresponding to the γ ray may be used to determine the tissue attenuation correction factor of the γ ray using the formula (2).

It is understood that the operations on a 3D CT image described herein including, for example, motion phase determination, correction, etc., may be performed on a 3D attenuation map corresponding to the 3D CT image. For instance, a 3D attenuation map including a plurality of 2D attenuation map layers may be generated based on the 3D CT image; subsequently, one or more operations including, for example, motion phase determination, correction, etc., may be performed on the 3D attenuation map or one or more of the plurality of 2D attenuation map layers of the 3D attenuation map to generate a processed 3D attenuation map, e.g., a corrected 3D attenuation map. In some embodiments, a 3D attenuation map may be generated by processing or modifying, based on an algorithm, voxel values of the voxels of the 3D CT image. A voxel value of a voxel of the 3D attenuation map may relate to the voxel value of the corresponding voxel of the 3D CT image based on the conversion algorithm.

Figure 6B:
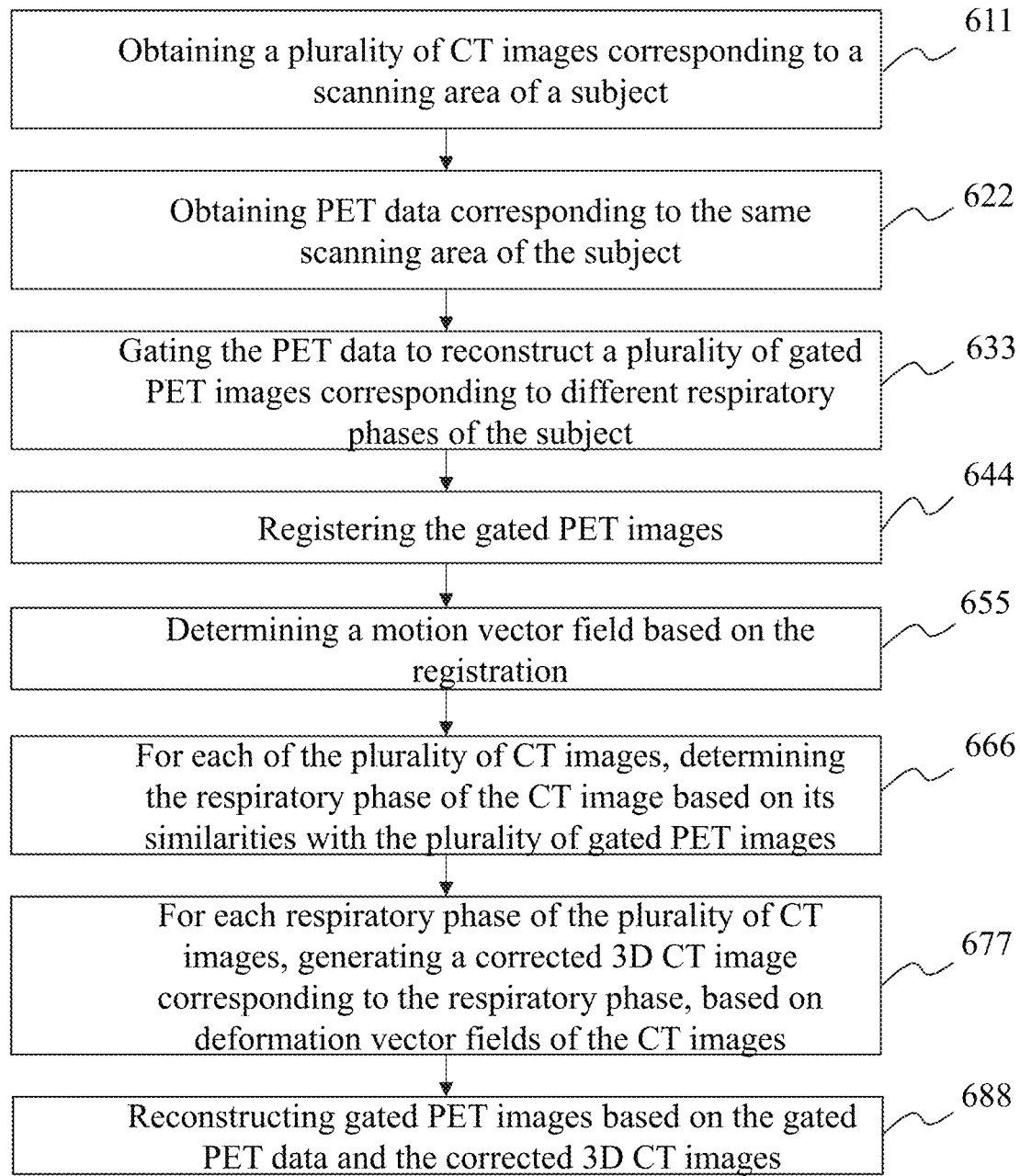

FIG. 6B is a flowchart illustrating an exemplary process for reconstructing a PET image according to some embodiments of the present disclosure. The operations of 611 through 666 may be similar to the operations of 610 through 660 respectively.

In 667, for each respiratory phase of the plurality of CT images, the processing module 440 may generate a corrected 3D CT image corresponding to the respiratory phase based on deformation vector fields of the CT images. As described in 667, each CT image (or CT image layer of a 3D CT image) may correspond to its respiratory phase. Any one of the respiratory phases may be determined as the reference phase that CT images with other respiratory phases may be corrected based on a deformation vector corresponding to the reference phase. Relate description may be found in the description of FIG. 6A. The processing module may generating the corrected 3D CT image with respect to the respiratory phase based on the corrected CT images. Therefore, 3D CT images may be generated corresponding to each respiratory phase, and further corresponding to a group of gated PET data with the same respiratory phase.

In 668, the processing module 440 may reconstruct gated PET images based on the gated PET data and the corrected 3D CT images. Since the relationship between the corrected 3D CT image and a group of gated PET data are determined in 677, the reconstruction unit 550 may reconstruct the gated PET images based on the groups of gated PET data and corresponding corrected 3D CT images.

Figure 7:
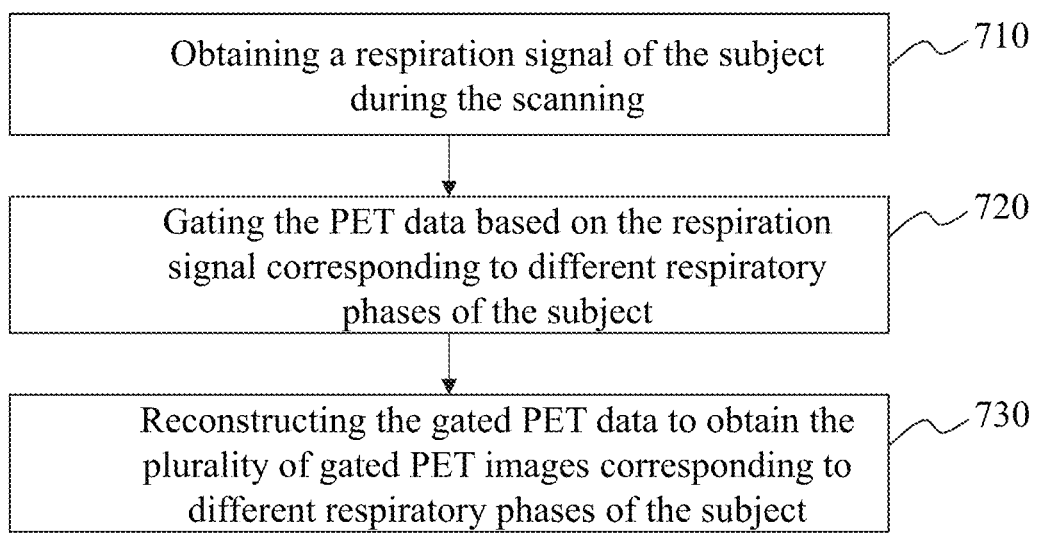
FIG. 7 is a flowchart illustrating an exemplary process for gating PET data according to some embodiments of the present disclosure.

FIG. 7 is a flowchart illustrating an exemplary process 700 for gating PET data according to some embodiments of the present disclosure. In some embodiments, process 700 may include obtaining a respiration signal of the subject during the scanning, gating the PET data based on the respiration signal, reconstructing the gated PET data to obtain the plurality of gated PET images corresponding to different respiratory phases of the subject. In some embodiments, one or more operations of process 700 for gating PET data may be implemented in the image processing system 100 illustrated in FIG. 1. For example, the process 700 may be stored in the storage module 420 of the data processing system 130 in the form of instructions, and invoked and/or executed by the data processing system 130 (e.g., the processor 230 of the data processing system 130).

In 710, the gating unit 510 may obtain the respiration signal of the subject during the scanning. In some embodiments, the respiratory signal may be obtained from the gating system 180. The gating system 180 may be used to collect information such as breathing information, heartbeat information etc., and analyze the information to obtain the gating parameter (e.g., the respiratory phase). In some embodiments, the respiratory signal may be approximated as described with respect to 630.

In 720, the gating unit 510 may gate the PET data based on the respiration signal. The respiratory signal may correspond to different respiratory phases of the subject. For example, the respiratory signal may correspond to N respiratory phases, wherein the N may be 1, 2, 5, 8, or any integer greater than 1. For example, the gating unit 510 may divide the respiratory signal into 4 respiratory phases, each of which may correspond to a different part in a cycle of the respiratory signal. The PET data may be gated or divided into groups (or frames) of gated PET data based on the 4 respiratory phases. Each group of gated PET data may correspond to one of the four respiratory phases.

In 730, the reconstruction unit 550 may reconstruct a plurality of gated PET image based on the gated PET data. In some embodiments, the reconstruction unit 550 may use a reconstruction algorithm to generate the plurality of gated PET images. Exemplary reconstruction algorithms may include an iterative reconstruction algorithm (e.g., a statistical reconstruction algorithm), a Fourier slice theorem algorithm, a filtered back projection (FBP) algorithm, a compressed sensing (CS) algorithm, a fan-beam reconstruction algorithm, a maximum likelihood expectation maximization (MLEM) algorithm, an ordered subset expectation maximization (OSEM) algorithm, a maximum a posterior (MAP)

algorithm, an analytic reconstruction algorithm, or the like, or any combination thereof. For example, the reconstruction unit 550 may generate the plurality of gated PET images using the statistical reconstruction algorithm or the MLEM algorithm.

In some embodiments, the number of the gated PET images corresponding to a respiratory cycle may equal the number of the respiratory phases. For example, if the respiratory signal is gated into 4 respiratory phases in a respiratory cycle, the PET data corresponding to a respiratory cycle may be divided into 4 groups of gated PET data, and the reconstruction unit 550 may reconstruct the 4 groups of gated PET data into 4 gated PET images corresponding to the 4 different respiratory phases.

Figure 8:
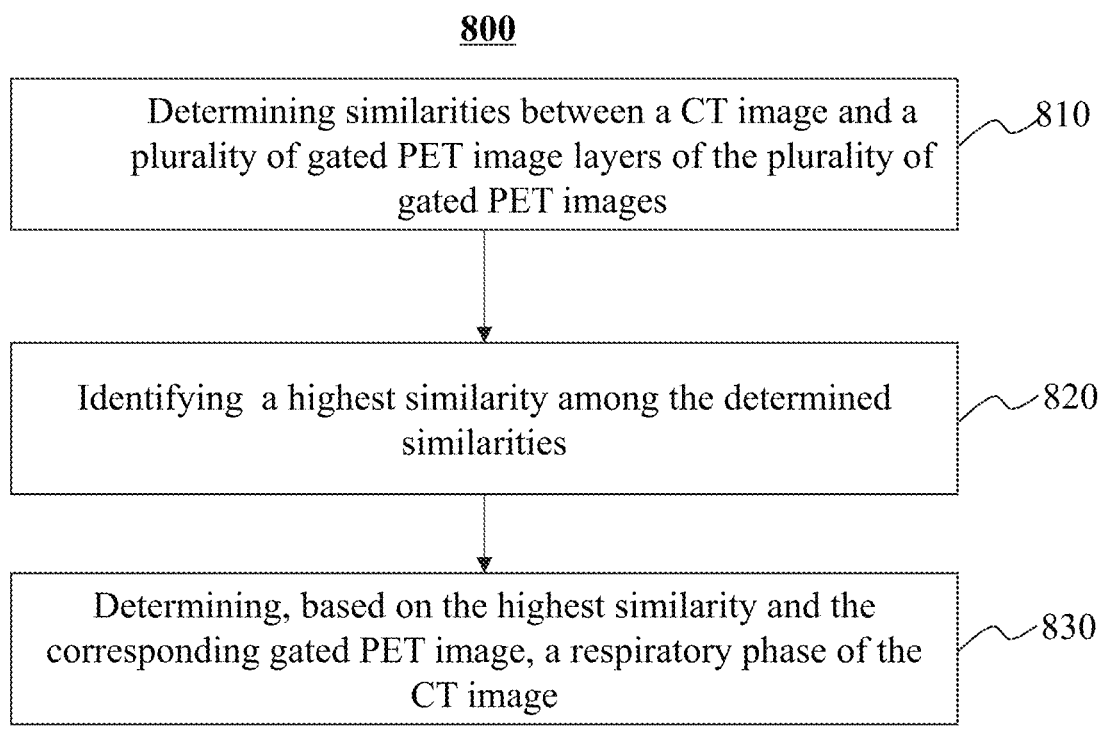
FIG. 8 is a flowchart illustrating an exemplary process for determining a respiratory phase of the CT image according to some embodiments of the present disclosure.

FIG. 8 is a flowchart illustrating an exemplary process 800 for determining a respiratory phase of a CT image layer according to some embodiments of the present disclosure. As shown in FIG. 8, the process 800 may include determining similarities between a CT image layer and a plurality of gated PET image layers, identifying the maximum similarity among the determined similarities, and determining a respiratory phase of the CT image layer. In some embodiments, one or more operations of process 800 for determining a respiratory phase of the CT image layer may be implemented in the image processing system 100 illustrated in FIG. 1. For example, the process 800 may be stored in the storage module 420 of the data processing system 130 in the form of instructions, and invoked and/or executed by the data processing system 130 (e.g., the processor 230 of the data processing system 130).

In 810, the motion phase determination unit 530 may determine similarities between a CT image layer and a plurality of gated PET image layers of a subject. In some embodiments, the similarity may include a pixel-based similarity, an entropy-based similarity, a mutual information similarity, or the like, or any combination thereof. The gated PET images may be 3D images with a same FOV as the 3D CT image. The 3D CT image and a gated 3D PET image may be expressed in a same coordinate system to facilitate the determination of the similarity of a CT image layer and a gated PET image layer there between. The same coordinate system may include an X axis, a Y axis, and a Z axis. The 3D CT image and the gated PET image may be expressed as C(x,y,z) and P(x,y,z,t), respectively, where t represents respiratory phase of the gated PET image. The coordinate (x,y,z) and the coordinate (x,y,z,t) may correspond to a same region of interest (ROI). For instance, the ROI may be the chest of the subject, and determined by a CT scanning system and a PET scanning system.

In some embodiments, the motion phase determination unit 530 may determine the mutual information similarity between each layer of the 3D CT image (e.g., an axial slice in the transverse plane of the 3D CT image) and a corresponding layer (e.g., also an axial slice in the transverse plane) of each of a plurality of gated PET images based on the function shown as formula (3):

$$\tau(z) = \underset{g}{\mathrm{argmax}}(D(C(x, y, z), P(x, y, z, g))), \tag{3}$$

where τ(z) represents the respiratory gate of a 3D CT image at slice z, D represents a measurement of similarity between the 3D CT image and the gated PET image, C(x,y,z) represents a 3D CT image, P(x,y,z,g) represents a gated PET image, x, y, and z represent coordinates of voxels in the 3D CT image and the gated PET image, and g represents a respiratory phase of the gated PET image. For a certain layer of the 3D CT image, the value of z is determined. The value of z of a corresponding layer of the gated PET image may be designated as the same of the CT image. Therefore, the 3D CT image C(x,y,z) and the gated PET image P(x,y,z,g) may be expressed as 2D images, and represented as a 2D CT image (or CT image layer) C(z), a gated PET image layer P(z,g). In some embodiments, z may be a value range that represents a cycle of the helical scanning of the CT scanning. During a cycle of the CT scanning, the radioactive scanning source 115 and the detector 112 may rotate 360 degrees. The C(x,y,z) may represent a 3D CT image as a portion of the whole 3D CT image. Correspondingly, the P(x,y,z,g) may represent a portion of the gated 3D PET image.

In some embodiments, the measurement of similarity D between the CT image layer and the gated PET image layer may be expressed as formula (4):

$$D(C(z),p(z,t))=H(C(z))+H(p(z,g))-H(C(z), p(z,g)), \tag{4}$$

where D(C(z), P(z,g)) represents mutual information between the CT image layer and the gated PET image layer, H(C(z)) represents an entropy of the CT image layer, H(P(z,g)) represents an entropy of the gated PET image layer, and H(C(z), P(z,g)) represents a combined entropy of the CT image layer and the gated PET image layer. In some embodiments, the entropy of the CT image H(C(z)), or the entropy of the gated PET image H(P(z,g)) may be determined by formula (5):

$$H(A)=-\int_0^{+\infty} p_A(v)\log(p_A(v))dv, \tag{5}$$

where H(A) represents the entropy of the CT image layer H(C(z)), or the entropy of the gated PET image layer H(P(z,g)), A represent an image, v represents an image pixel value in image A, and $p_A(v)$ represent a histogram of the image A. In some embodiments, $p_A(v)$ is determined by formula (6):

$$p_A(v)=\iint_{All}\delta(A(x,y)-v)dxdy, \tag{6}$$

where A(x,y) is the pixel value at (x,y), δ represents a window function centered at 0 (e.g., a Gaussian function with mean 0). The pixel value at (x,y) may be the gray value of the pixel at (x,y).

In some embodiments, the combined entropy of the gated PET image layer H(C(z),P(z,g)) may be determined by formula (7):

$$H(A,B)=-\iint_0^{+\infty} p_{A,B}(v,u))\log(p_{A,B}(v,u)dudv, \tag{7}$$

where A and B represent two images, respectively. H(A,B) represents the combined entropy of image A and image B, u represents image pixel value in image A, v represents an image pixel value in image B, and $p_{A,B}(v,u)$ is a combined histogram of image A and image B, and may be determined by formula (8):

$$p_{A,B}(v,u)=\iint_{All}\delta(A(x,y)-v)\delta(B(x,y)-u)dxdy, \tag{8}$$

where δ represents a window function centered at 0. In some embodiments, the function δ in the formula (6) and the formula (8) may take the form of the Dirac delta function, as determined by formulae (9) and (10):

$$\delta(x) = \begin{cases} +\infty, & x = 0 \\ 0, & x \neq 0 \end{cases}. \tag{9}$$

which is constrained to satisfy the identity:

$\int_{-\infty}^{+\infty} \delta(x)dx = 1.$ (10)

In 820, the motion phase determination unit 530 may identify a highest or maximum similarity among the determined similarities. In some embodiments, the motion phase determination unit 530 may rank the similarities from the lowest similarity to the highest similarity. The highest similarity may be identified by the motion phase determination unit 530. For example, the determined similarities may include 0.6, 0.5, 0.3, and 0.9. The motion phase determination unit 530 may rank the similarities as 0.3, 0.5, 0.6, and 0.9, and identify 0.9 as the highest similarity.

In 830, the motion phase determination unit 530 may further determine a respiratory phase of the CT image layer based on the highest similarity and the corresponding gated PET image layer that exhibits the highest similarity with the CT image layer. In some embodiments, the respiratory phase of the corresponding gated PET image layer that has the highest similarity with the CT image layer may be designated as the respiratory phase of the CT image layer.

Figure 9:
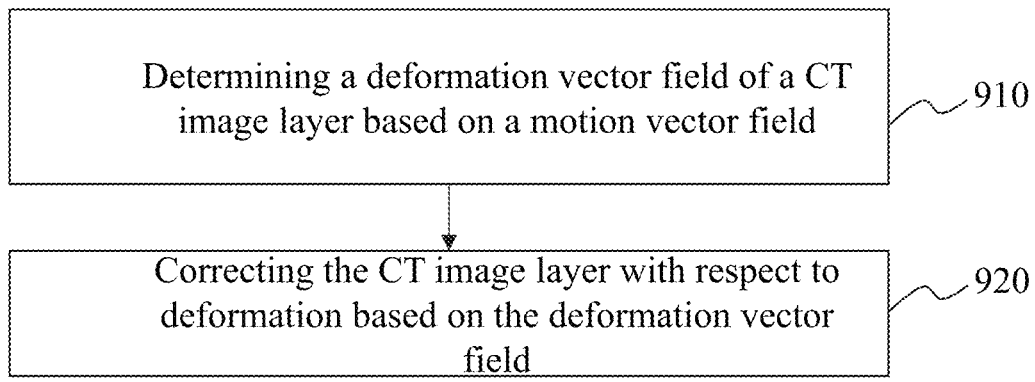
FIG. 9 is a flowchart illustrating an exemplary process for correcting the CT image according to some embodiments of the present disclosure.

FIG. 9 is a flowchart illustrating an exemplary process 900 for correcting a CT image layer according to some embodiments of the present disclosure. As shown in FIG. 9, the process 900 may include determining a deformation vector field of a CT image layer based on a motion vector field, and correcting the CT image layer with respect to deformation based on the deformation vector field. In some embodiments, one or more operations of process 900 for correcting a CT image layer may be implemented in the image processing system 100 illustrated in FIG. 1. For example, the process 900 may be stored in the storage module 420 of the data processing system 130 in the form of instructions, and invoked and/or executed by the data processing system 130 (e.g., the processor 230 of the data processing system 130).

In 910, the motion deformation processing unit 540 may determine a deformation vector field of a CT image layer based on a motion vector field and the determined respiratory phase of the CT image layer. The deformation vector field may include a plurality of deformation vectors. A deformation vector may be a 2D vector, 3D vector, or an N-dimensional vector. In some embodiments, the deformation vector field of the CT image layer may be determined based on a motion vector field of a gated PET image layer that has the same respiration phase with the CT image layer.

In some embodiments, the deformation vector field may be determined based on the motion vector field of the corresponding gated PET image that includes the gated PET layer having the highest similarity with CT image layer. The motion vector filed from respiratory phase t to reference frame may be expressed as $(m_u(x,y,z,t), m_v(x,y,z,t), m_w(x,y,z,t))$, where $m_u$ represents the motion vector component in the x axis direction, $m_v$ represents the motion vector component in the y axis direction, $m_w$ represents the motion vector component in the z axis direction, and t represents the respiratory phase. The deformation vector field of the 3D CT image at slice z may be expressed as $(m_u(x,y,z,\tau(z)), m_v(x,y,z,\tau(z)), m_w(x,y,z,\tau(z)))$, where $m_u(x,y,z,\tau(z))$ represents the deformation vector component in the x axis direction, $m_v(x,y,z,\tau(z))$ represents the deformation vector component in the y axis direction, $m_w(x,y,z,\tau(z))$ represents the deformation vector component in the in the z axis direction, and $\tau(z)$ represents the respiratory phase of the CT image layer. For example, the respiration phase of the CT image layer $\tau(z)$ may correspond to a 4th respiratory phase of the corresponding gated PET image layer by the formula (3). The deformation vector field of the CT image layer may be determined as $(m_u(x,y,z,4), m_v(x,y,z,4), m_w(x,y,z,4))$ that may be the same as the motion vector field of the corresponding gated PET image layer relative to the reference gated PET image corresponding to a reference motion phase (e.g., the gated PET image corresponding to a first respiratory phase of a respiratory motion) as described elsewhere in the present disclosure. The deformation vector field of the CT image layer so determined is also considered relative to the same reference motion phase.

In 920, the motion deformation processing unit 540 may correct the CT image layer with respect to deformation based on the deformation vector field. In some embodiment, the respiratory phase of the CT image layer may be the same as the respiratory phase of the gated PET image layer having the highest similarity with the CT image layer. The motion deformation processing unit 540 may correct the CT image layer based on the determined deformation vector field, and generate the corrected CT image layer using formula (11):

$$C_{ref}(x,y,z) = C(x+m_u(x,y,z,\tau(z)), y+m_v(x,y,z,\tau(z)), z+m_w(x,y,z,\tau(z))), \quad (11)$$

where $C_{ref}(x,y,z)$ represents the corrected CT image layer at the reference frame.

EXAMPLES

The examples are provided for illustration purposes, and not intended to limit the scope of the present disclosure.

Example 1

Figure 10A:
FIG. 10A and FIG. 10B illustrate exemplary CT images with artifacts according to some embodiments of the present disclosure.
Figure 10B:
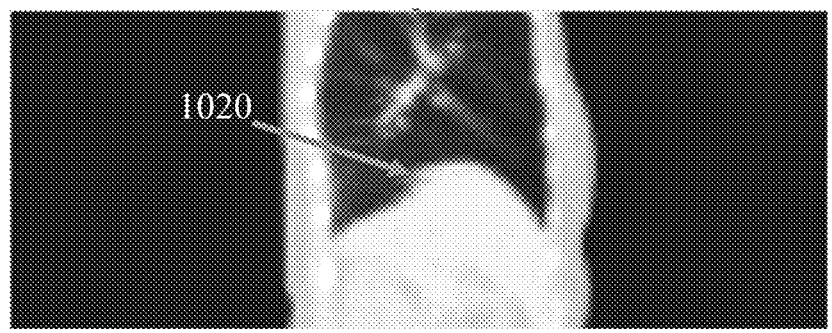

FIG. 10A and FIG. 10B illustrate exemplary CT image layers with artifacts according to some embodiments of the present disclosure. FIG. 10A and FIG. 10B show, respectively, a coronal slice and a sagittal slice of a 3D CT image obtained by scanning the thorax of a patient. The patient lied on the back and breathed freely during the scan. As illustrated, the coronal slice of the 3D CT image in FIG. 10A shows artifacts 1010, and the sagittal slice in FIG. 10B shows artifacts 1020. The artifacts may be caused by a shift of the lung and liver of the subject due to respiratory motion during the CT scan. The artifact 1010 and artifact 1020 are located at an upper part of the liver. The artifact 1010 and/or artifact 1020 may decrease the quality of the CT image and the PET image reconstructed with this CT image for attenuation correction, hence affecting the diagnosis of the patient by a user (e.g., a doctor).

Example 2

FIG. 11A-1 through FIG. 11A-3 and FIG. 11B-1 through FIG. 11B-3 illustrate gated PET images of two different respiratory phases reconstructed overlapped with the same attenuation map without correction according to some embodiments of the present disclosure. The two gated PET images correspond to two different respiratory phases, an end-inspiratory phase (EIP) and an end-expiratory phase (EEP). The attenuation map corresponds to a 3D CT image without correction obtained from a helical CT scan during which the subject breathed normally.

Figures 1, 11A:
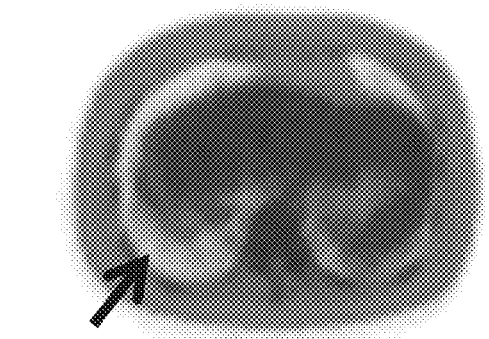
Figures 1, 11B:
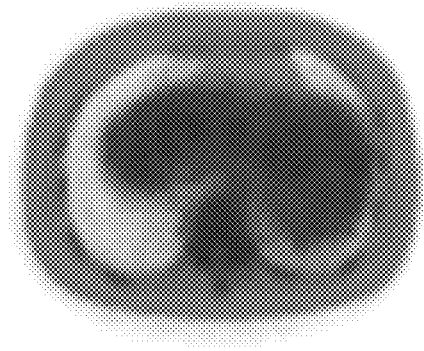
Figures 2, 11A:
Figures 2, 11B:
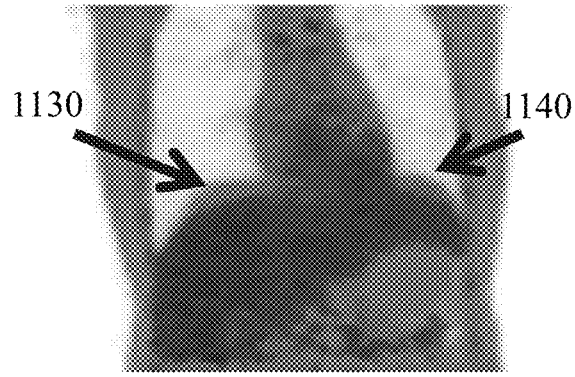
Figures 3, 11A:
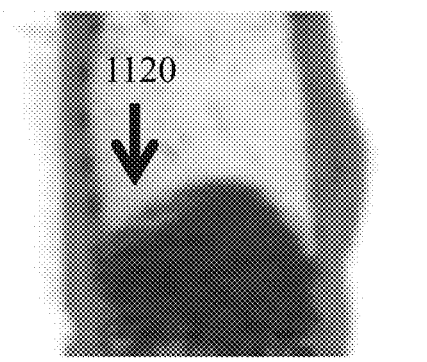
Figures 3, 11B:
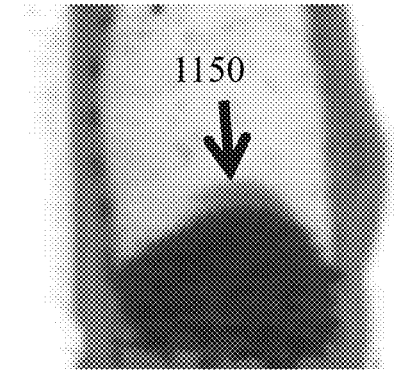

FIG. 11A-1 through FIG. 11A-3 correspond to the EEP. FIG. 11B-1 through FIG. 11B-3 correspond to the EIP. FIG. 11A-1 and FIG. 11B-1 are transverse slices of the gated PET images corresponding to the EEP and the EIP, respectively. FIG. 11A-2 and FIG. 11B-2 are coronal slices of the gated PET images corresponding to the EEP and the EIP, respectively. FIG. 11A-3 and FIG. 11B-3 are sagittal slices of the gated PET images corresponding to the EEP and the EIP, respectively.

As shown in the FIG. 11A-1 through FIG. 11A-3, the dome of the liver matches well with the attenuation map, while there is a mismatch at the lower part of the liver between the PET image and the attenuation map indicated by 1110 and 1120. As shown in the FIG. 11B-1 through FIG. 11B-3, the lower part of the liver matches well with the attenuation map, while there is a mismatch at the top of the liver between the PET image and the attenuation map indicated by 1130, 1140, and 1150.

Example 3

Figure 12:
FIG. 12 illustrate the results of slice-wise respiratory phase determination on an attenuation map obtained from an uncorrected 3D CT image according to some embodiments of the present disclosure.

FIG. 12 illustrate the results of slice-wise respiratory phase determination on an attenuation map obtained from an uncorrected 3D CT image according to some embodiments of the present disclosure. FIG. 12 shows a coronal slice of the attenuation map. Different transversal image layers are labeled as 1210, 1220, 1230, 1240, 1250 . . . 1290. Respiratory gate number (also referred as the phase number) for the image layers may be obtained by determining image similarity between the transversal image layers with corresponding layers in a gated PET image as described in 660. Each of the CT image layers 1210 through 1290 corresponds to a gate number representing a respiratory phase. The CT image layers 1210 and 1290 correspond to Gate 1. The CT image layers 1220 and 1280 correspond to Gate 2. The CT image layers 1230 and 1270 correspond to Gate 3. The CT image layers 1240 and 1260 correspond to Gate 4. The CT image layer 1250 corresponds to Gate 5. A same gating number in FIG. 12 indicates a same motion amplitude (or a same range of motion amplitude) occurring in an inspiratory phase or in an expiratory phase.

Example 4

Figures 1, 13A:
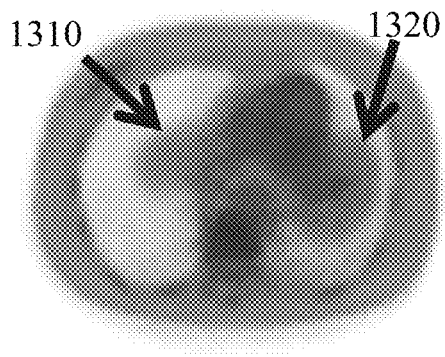

FIG. 13A-1 through FIG. 13A-3 and FIG. 13B-1 through FIG. 13B-3 illustrate a gated PET image overlapped with an attenuation map without correction and with a corrected attenuation map, respectively, according to some embodiments of the present disclosure. FIG. 13A-1 is a slice of the gated PET image and attenuation map in the transverse plane. FIG. 13A-2 is a slice of the gated PET image and attenuation map in the coronal plane. FIG. 13A-3 is a slice of the gated PET image and attenuation map in the sagittal plane. As shown in FIG. 13A-1 through FIG. 13A-3, the dome of the liver does not match the attenuation map. See, e.g., the mismatch indicated by 1310, 1320, 1330, 1340, and 1350.

Figures 1, 13B:
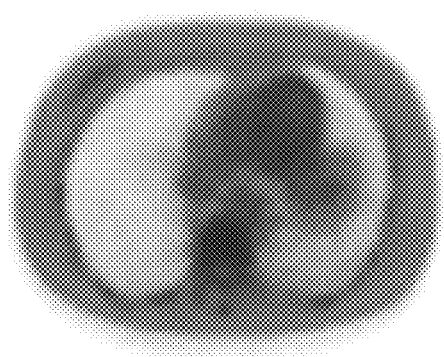
Figures 2, 13A:
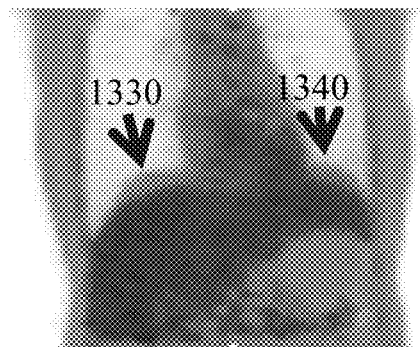
Figures 2, 13B:
Figures 3, 13A:
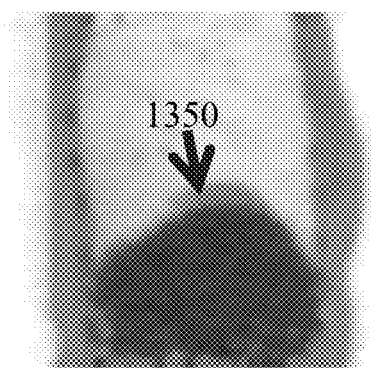
Figures 3, 13B:
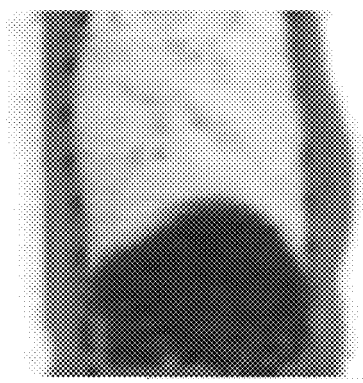

FIG. 13A-1 through FIG. 13A-3 and FIG. 13B-1 through FIG. 13B-3 illustrate a gated PET image overlapped with an attenuation map without correction and with a corrected attenuation map, respectively, according to some embodiments of the present disclosure. The corrected 3D CT image used in FIG. 13B-1 through FIG. 13B-3 and the 3D CT image without correction used in FIG. 13A-1 through FIG. 13A-3 were based on data from a same CT scan. FIG. 13B-1 is a slice of the gated PET image and attenuation map in the transverse plane. FIG. 13B-2 is a slice of the gated PET image and attenuation map in the coronal plane. FIG. 13B-3 is a slice of the gated PET image and attenuation map in the sagittal plane. As show in the FIG. 13B-1 through FIG. 13B-3, the mismatch of the gated PET image and the CT image was reduced, compared to that shown in FIG. 13A-1 through FIG. 13A-3.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code code, etc.) or combining software and hardware implementation that may all generally be referred to herein as a "block," "module," "module," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities of ingredients, properties such as molecular weight, reaction conditions, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. An imaging method implemented on at least one machine each of which has at least one processor and storage, the method comprising:
    obtaining a 3D CT image of a scanning area of a subject;
    generating an attenuation map by processing voxel values of a plurality of voxels of the 3D CT image, a voxel value of a voxel of the attenuation map relating to a voxel value of a corresponding voxel of the 3D CT image;
    obtaining PET data of the scanning area of the subject, the PET data corresponding to a first motion signal with a plurality of motion phases of the subject;
    gating the PET data based on the plurality of motion phases of the first motion signal;
    reconstructing, based on the gated PET data, a plurality of gated 3D PET images, a gated 3D PET image corresponding to one of the plurality of motion phases, a gated 3D PET image including a plurality of gated PET image layers, a gated PET image layer corresponding to a group of spatial points relating to the subject;
    determining, based on the plurality of gated 3D PET images, a motion vector field corresponding to a gated 3D PET image of the plurality of gated 3D PET images, a motion vector field corresponding to a motion phase;
    determining a plurality of motion phases for the attenuation map based on the motion phases of the plurality of gated 3D PET images;
    correcting the attenuation map based on a plurality of motion vector fields of the plurality of gated 3D PET images; and
    reconstructing a gated PET image based on the corrected attenuation map and the PET data.

2. The method of claim 1, wherein the determining, based on the plurality of gated 3D PET images, a motion vector field corresponding to a gated 3D PET image of the plurality of gated 3D PET images comprises:
    registering the plurality of gated 3D PET images with a reference 3D PET image; and
    determining, based on the registration, a motion vector field corresponding to a gated 3D PET image of the plurality of gated 3D PET images.

3. The method of claim 2, wherein the registering the plurality of gated 3D PET images with a reference 3D PET image is based on at least one of an optical flow registration algorithm, demons registration algorithm, or a B-spline registration algorithm.

4. The method of claim 1, wherein the attenuation map includes a plurality of attenuation map layers, an attenuation map layer corresponding to a group of spatial points relating to the subject, and the determining a plurality of motion phases for the attenuation map based on the motion phases of the plurality of gated 3D PET images comprises:

for each of the plurality of attenuation map layers, identifying, from each of the plurality of gated 3D PET images, a gated PET image layer corresponding to a same group of spatial points as the attenuation map layer;
determining a similarity between the attenuation map layer and each of the plurality of identified gated PET image layers; and
designating one of the motion phases of the plurality of gated 3D PET images as the motion phase of the attenuation map layer based on its similarities with the plurality of identified gated PET image layers.

5. The method of claim 4, wherein the designating one of the motion phases of the plurality of gated 3D PET images as the motion phase of the attenuation map layer based on its similarities with the plurality of identified gated PET image layers comprises:
identifying a highest similarity among the determined similarities between the attenuation map layer and the plurality of identified gated PET image layers; and
designating the motion phase of the gated 3D PET image including the identified gated PET image layer having the highest similarity as the motion phase of the attenuation map layer.

6. The method of claim 4, wherein the determining the similarity between the attenuation map layer and each of the plurality of identified gated PET image layers is based on at least one of a pixel-based similarity, an entropy-based similarity, a mutual information similarity, or a contour-based similarity.

7. The method of claim 1, wherein the determining a plurality of motion phases for the attenuation map based on the motion phases of the plurality of gated 3D PET images comprises:
obtaining a second motion signal during a scan that provides the 3D CT image, wherein the second motion signal is of a same type or transformed to a same type as the first motion signal; and
determining the plurality of motion phases of the attenuation map based on the motion phases of the plurality of gated 3D PET images and the second motion signal.

8. The method of claim 7, wherein the second motion signal is obtained from an external device.

9. The method of claim 1, wherein the plurality of motion phases of the first motion signal are determined based on an amplitude or a time interval of a motion presented in the first motion signal.

10. The method of claim 1, wherein the first motion signal is obtained based on the PET data or from an external device.

11. The method of claim 1, wherein the attenuation map includes a plurality of attenuation map layers, and the correcting the attenuation map includes:
for each of the plurality of attenuation map layers, determining a deformation vector field for the attenuation map layer based on the motion vector field of the gated 3D PET image corresponding to the same motion phase as the attenuation map layer with respect to a gated 3D PET image corresponding to a reference motion phase; and
correcting the attenuation map layer with respect to the reference motion phase based on the deformation vector field.

12. The method of claim 11, wherein the reference motion phase is one of the plurality of motion phases of the subject.

13. The method of claim 1, wherein the motion vector field includes a plurality of motion vectors, the motion vector representing a motion of a spatial point of the subject from a gated 3D PET image to another gated 3D PET image.

14. A system comprising:
at least one storage device storing a set of instructions;
at least one processor in communication with the at least one storage device, wherein when executing the set of instructions, the at least one processor is configured to cause the system to perform operations including:
obtaining a 3D CT image of a scanning area of a subject;
generating an attenuation map by processing voxel values of a plurality of voxels of the 3D CT image, a voxel value of a voxel of the attenuation map relating to a voxel value of a corresponding voxel of the 3D CT image;
obtaining PET data of the scanning area of the subject, the PET data corresponding to a first motion signal with a plurality of motion phases of the subject;
gating the PET data based on the plurality of motion phases of the first motion signal;
reconstructing, based on the gated PET data, a plurality of gated 3D PET images, a gated 3D PET image corresponding to one of the plurality of motion phases, a gated 3D PET image including a plurality of gated PET image layers, a gated PET image layer corresponding to a group of spatial points relating to the subject;
determining, based on the plurality of gated 3D PET images, a motion vector field corresponding to a gated 3D PET image of the plurality of gated 3D PET images, a motion vector field corresponding to a motion phase;
determining a plurality of motion phases for the attenuation map based on the motion phases of the plurality of gated 3D PET images;
correcting the attenuation map based on a plurality of motion vector fields of the plurality of gated 3D PET images; and
reconstructing a gated PET image based on the corrected attenuation map and the PET data.

15. The system of claim 14, wherein the determining, based on the plurality of gated 3D PET images, a motion vector field corresponding to a gated 3D PET image of the plurality of gated 3D PET images comprises:
registering the plurality of gated 3D PET images with a reference 3D PET image; and
determining, based on the registration, a motion vector field corresponding to a gated 3D PET image of the plurality of gated 3D PET images.

16. The system of claim 14, wherein the attenuation map includes a plurality of attenuation map layers, an attenuation map layer corresponding to a group of spatial points relating to the subject, and the determining a plurality of motion phases for the attenuation map based on the motion phases of the plurality of gated 3D PET images comprises:
for each of the plurality of attenuation map layers, identifying, from each of the plurality of gated 3D PET images, a gated PET image layer corresponding to a same group of spatial points as the attenuation map layer;
determining a similarity between the attenuation map layer and each of the plurality of identified gated PET image layers; and
designating one of the motion phases of the plurality of gated 3D PET images as the motion phase of the attenuation map layer based on its similarities with the plurality of identified gated PET image layers.

17. The system of claim 14, wherein the determining a plurality of motion phases for the attenuation map based on the motion phases of the plurality of gated 3D PET images comprises:

obtaining a second motion signal during a scan that provides the 3D CT image, wherein the second motion signal is of a same type or transformed to a same type as the first motion signal; and determining the plurality of motion phases of the attenuation map based on the motion phases of the plurality of gated 3D PET images and the second motion signal.

18. The system of claim 14, wherein the attenuation map includes a plurality of attenuation map layers, and the correcting the attenuation map includes:

for each of the plurality of attenuation map layers, determining a deformation vector field for the attenuation map layer based on the motion vector field of the gated 3D PET image corresponding to the same motion phase as the attenuation map layer with respect to a gated 3D PET image corresponding to a reference motion phase; and correcting the attenuation map layer with respect to the reference motion phase based on the deformation vector field.

19. The system of claim 18, wherein the reference motion phase is one of the plurality of motion phases of the subject.

20. A non-transitory computer-readable storage medium, comprising at least one set of instructions, wherein when executed by at least one processor of a computing device, the at least one set of instructions direct the at least one processor to perform operations including:

obtaining a 3D CT image of a scanning area of a subject;

generating an attenuation map by processing voxel values of a plurality of voxels of the 3D CT image, a voxel value of a voxel of the attenuation map relating to a voxel value of a corresponding voxel of the 3D CT image;

obtaining PET data of the scanning area of the subject, the PET data corresponding to a first motion signal with a plurality of motion phases of the subject;

gating the PET data based on the plurality of motion phases of the first motion signal;

reconstructing, based on the gated PET data, a plurality of gated 3D PET images, a gated 3D PET image corresponding to one of the plurality of motion phases, a gated 3D PET image including a plurality of gated PET image layers, a gated PET image layer corresponding to a group of spatial points relating to the subject;

determining, based on the plurality of gated 3D PET images, a motion vector field corresponding to a gated 3D PET image of the plurality of gated 3D PET images, a motion vector field corresponding to a motion phase;

determining a plurality of motion phases for the attenuation map based on the motion phases of the plurality of gated 3D PET images;

correcting the attenuation map based on a plurality of motion vector fields of the plurality of gated 3D PET images; and reconstructing a gated PET image based on the corrected attenuation map and the PET data.

* * * * *